United States Patent
Atienza et al.

(10) Patent No.: US 10,221,260 B2
(45) Date of Patent: Mar. 5, 2019

(54) PHENOLATE TRANSITION METAL COMPLEXES, PRODUCTION AND USE THEREOF

(71) Applicant: ExxonMobil Chemical Patents Inc., Baytown, TX (US)

(72) Inventors: Crisita Carmen H. Atienza, Houston, TX (US); David A. Cano, Houston, TX (US); Catherine A. Faler, Houston, TX (US); Kevin P. Ramirez, West Lafayette, IN (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/644,492

(22) Filed: Jul. 7, 2017

(65) Prior Publication Data

US 2018/0030167 A1    Feb. 1, 2018

Related U.S. Application Data

(60) Provisional application No. 62/368,247, filed on Jul. 29, 2016.

(51) Int. Cl.
| | |
|---|---|
| C08F 10/02 | (2006.01) |
| C07F 7/00 | (2006.01) |
| C07D 209/86 | (2006.01) |
| C08F 10/06 | (2006.01) |
| C07C 43/23 | (2006.01) |
| C08F 110/06 | (2006.01) |

(52) U.S. Cl.
CPC .............. *C08F 10/02* (2013.01); *C07C 43/23* (2013.01); *C07D 209/86* (2013.01); *C07F 7/00* (2013.01); *C08F 10/06* (2013.01); *C08F 110/06* (2013.01); *C08F 2410/01* (2013.01)

(58) Field of Classification Search
None
See application file for complete search history.

(56) References Cited

U.S. PATENT DOCUMENTS

| | | | |
|---|---|---|---|
| 6,232,421 B1 | 5/2001 | Fujita et al. | |
| 6,333,389 B2 | 12/2001 | Whiteker et al. | |
| 6,333,423 B1 | 12/2001 | Kol et al. | |
| 6,596,827 B2 | 7/2003 | Kol et al. | |
| 6,841,502 B2 | 1/2005 | Boussie et al. | |
| 7,812,104 B2 | 10/2010 | Canich et al. | |
| 8,071,701 B2 | 12/2011 | Klosin et al. | |
| 8,383,753 B2 | 2/2013 | Kiosin et al. | |
| 8,609,794 B2 | 12/2013 | Klosin et al. | |
| 8,791,217 B2 | 7/2014 | Hlavinka et al. | |
| 8,907,032 B2 | 12/2014 | Kol et al. | |
| 8,937,137 B2 | 1/2015 | Holtcamp et al. | |
| 8,952,114 B2 | 2/2015 | Giesbrecht et al. | |

(Continued)

FOREIGN PATENT DOCUMENTS

| | | |
|---|---|---|
| WO | 00/16763 | 3/2000 |
| WO | 00/39064 | 7/2000 |

(Continued)

OTHER PUBLICATIONS

Cohen et al., "Propylene Polymerization by C1-Symmetric {ONNO'}-Type Salan Zirconium Complexes," Journal of Polymer Science Part A: Polymer Chemistry, 2013, vol. 51, pp. 593-600.

(Continued)

*Primary Examiner* — Catherine S Branch

(57) ABSTRACT

Phenolate ligands and transition metal complexes are disclosed for use in alkene polymerization, with optional chain transfer agent, to produce polyolefins.

35 Claims, 13 Drawing Sheets

Ball and stick model of 1-Zr.

(56) References Cited

U.S. PATENT DOCUMENTS

| | | |
|---|---|---|
| 8,957,171 B2 | 2/2015 | Giesbrecht et al. |
| 8,957,172 B2 | 2/2015 | Giesbrecht et al. |
| 9,000,108 B2 | 4/2015 | Klosin et al. |
| 9,045,568 B2 | 6/2015 | Giesbrecht et al. |
| 9,150,676 B2 | 10/2015 | Kol et al. |
| 9,193,813 B2 | 11/2015 | Kol et al. |
| 9,200,099 B2 | 12/2015 | Kol et al. |
| 9,200,100 B2 | 12/2015 | Kol et al. |
| 9,290,589 B2 | 3/2016 | Evans et al. |
| 9,365,661 B2 | 6/2016 | Giesbrecht et al. |
| 9,382,349 B2 | 7/2016 | Harrington et al. |
| 9,422,383 B2 | 8/2016 | LiPiShan et al. |
| 9,534,070 B2 | 1/2017 | Spencer et al. |
| 2004/0132789 A1 | 7/2004 | Bergeron |
| 2006/0024517 A1 | 2/2006 | Doan et al. |
| 2006/0025548 A1 | 2/2006 | Boussie et al. |
| 2006/0052554 A1 | 3/2006 | Boussie et al. |
| 2015/0291713 A1 | 10/2015 | Klosin et al. |
| 2015/0337062 A1 | 11/2015 | Demirors et al. |
| 2015/0344601 A1 | 12/2015 | Demirors et al. |
| 2016/0280722 A1 | 8/2016 | Atienza et al. |
| 2017/0096509 A1 | 4/2017 | Atienza et al. |

FOREIGN PATENT DOCUMENTS

| | | |
|---|---|---|
| WO | 01/21684 | 3/2001 |
| WO | 02/36638 | 5/2002 |
| WO | 03/091262 | 11/2003 |
| WO | 2005/108406 | 11/2005 |
| WO | 2006/020624 | 2/2006 |
| WO | 2007/130306 | 11/2007 |
| WO | 2012/027448 | 3/2012 |
| WO | 2012/098521 | 7/2012 |
| WO | 2012/111779 | 8/2012 |
| WO | 2013/096573 | 6/2013 |
| WO | 2014/022008 | 2/2014 |
| WO | 2014/022010 | 2/2014 |
| WO | 2014/022011 | 2/2014 |
| WO | 2014/022012 | 2/2014 |
| WO | 2014/022746 | 2/2014 |
| WO | 2014/070502 | 5/2014 |
| WO | 2014/143202 | 9/2014 |
| WO | 2015/088819 | 6/2015 |
| WO | 2016/003878 | 1/2016 |
| WO | 2016/003879 | 1/2016 |
| WO | 2016/089935 | 6/2016 |
| WO | 2016/094861 | 6/2016 |
| WO | 2016/094866 | 6/2016 |

OTHER PUBLICATIONS

Cohen et al., "Same Ligand, Different Metals: Diiodo-Salan Complexes of the Group 4 Triad in Isospecific Polymerization of 1-Hexene and Propylene," Macromolecules, 2010, vol. 43, No. 4, pp. 1689-1691.

Cohen et al., "C1-Symmetric Zirconium Complexes of [ONNO']-Type Salan Ligands: Accurate Control of Catalyst Activity, Isospecificity, and Molecular Weight in 1-Hexene Polymerization," Organometallics, 2009, vol. 28, No. 5, pp. 1391-1405.

Groysman et al., "High Molecular Weight Atactic Polypropylene Prepared by Zirconium Complexes of an Amine Bis(phenolate) Ligand," Israel Journal of Chemistry, 2002, vol. 42, pp. 373-381.

Hustad et al., "Continuous Production of Ethylene-Based Diblock Copolymers Using Coordinative Chain Transfer Polymerization," Macromolecules, 2007, vol. 40, No. 20, pp. 7061-7064.

Kiesewetter et al., "Stereospecific Octahedral Group 4 Bis(phenolate) Ether Complexes for Olefin Polymerization," Journal of the American Chemical Society, 2010, vol. 132, No. 16, pp. 5566-5567.

Kiesewetter et al., "Octahedral Group IV Bis(phenolate) Catalysts for 1-Hexene Homopolymerization and Ethylene/1-Hexene Copolymerization," Macromolecules, 2013, vol. 46, No. 7, pp. 2569-2575.

Nakata et al., "Controlled Isospecific Polymerization of alpha-Olefins by Hafnium Complex Incorporating with a trans-Cyclooctanediyl-Bridged [OSSO]-Type Bis(phenolate) Ligand," Macromolecules, 2013, vol. 46, No. 17, pp. 6758-6764.

Reybuck et al., "Amine Bis(phenolate) Zirconium Complexes: Influence of Ligand Structure and Cocatalyst on Copolymerization Behavior," Macromolecules, 2005, vol. 38, No. 7, pp. 2552-2558.

Segal et al., "Zirconium and Titanium Diamine Bis(phenolate) Catalysts for alpha-Olefin Polymerization: From Atactic Oligo(1-hexane) to Ultrahigh-Molecular-Weight Isotactic Poly(1-hexene)," Organometallics, 2005, vol. 24, No. 2, pp. 200-202.

Tshuva et al., "Novel zirconium complexes of amine bis(phenolate) ligands. Remarkable reactivity in polymerization of hex-1-ene due to an extra donor arm," Chemical Communication, The Royal Society of Chemistry, 2000, pp. 379-380.

Tshuva et al., "[ONNO]-Type Amine Bis(phenolate) Zirconium and Hafnium Complexes as Extremely Active 1-Hexene Polymerization Catalysts," Organometallics, 2002, vol. 21, pp. 662-670.

Tshuva et al., "Zirconium Complexes of Amine-Bis(phenolate) Ligands as Catalysts for 1-Hexene Polymerization: Peripheral Structural Parameters Strongly Affect Reactivity," Organometallics, 2001, vol. 20, pp. 3017-3028.

Tshuva et al., "Isospecific Living Polymerization of 1-Hexene by a Readily Available Nonmetallocene C2-Symmetrical Zirconium Catalyst," Journal of the American Chemical Society, 2000, vol. 122, No. 43, pp. 10706-10707.

Jain et al., "Antithrombotic Activity of a Newly Synthesized Coumarin Derivative 3-(5-hydroxy-2,2-dimethylchroman-6-yl)-N-{2-[3-(5-hydroxy-2,2-dimethylchroman-6-yl)propioylamino]ethyl}propionamide," Chemical Biology & Drug Design, 2013, vol. 81, No. 4, pp. 499-508.

Ball and stick model of 1-Zr.

Compound A-6 in CD2Cl2; 1H NMR spectrum

Compound B-4 in CD2Cl2; 1H NMR spectrum

Compound 1-Hf in CD2Cl2; 1H NMR spectrum

Compound 2-Zr in CD2Cl2; 1H NMR spectrum

Compound 2-Hf in CD2Cl2; 1H NMR spectrum

FIGURE 10
GPC data for Table 1, Entry 25 (catalyst = 1-Zr; polymer = HDPE)
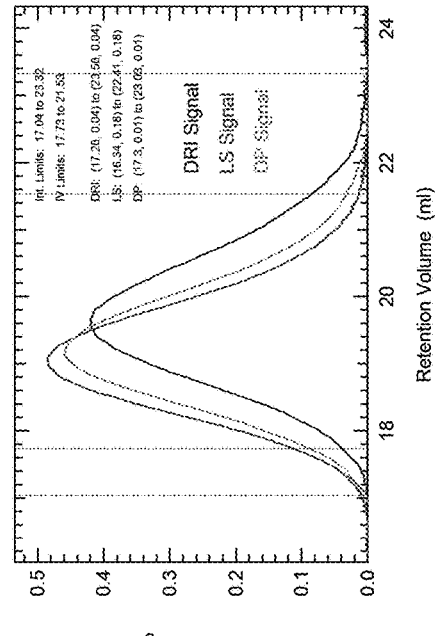
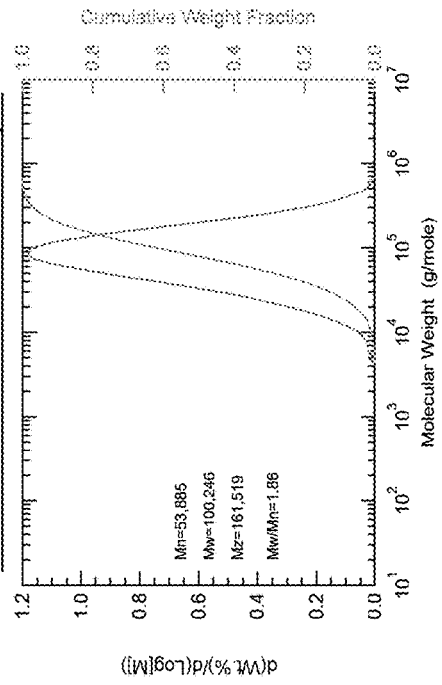
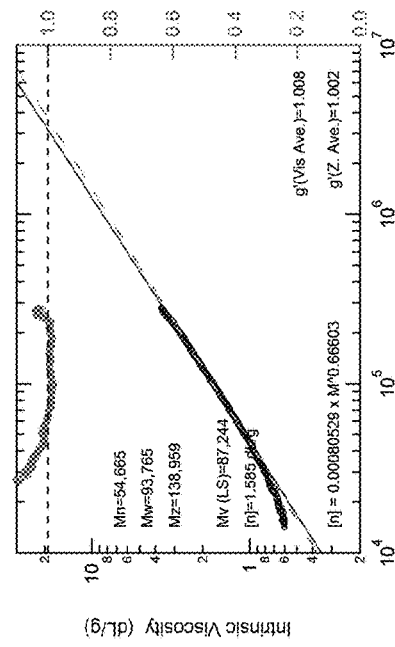

FIGURE 11
GPC data for Table 1, Entry 27 (catalyst = 1-Hf; polymer = HDPE)
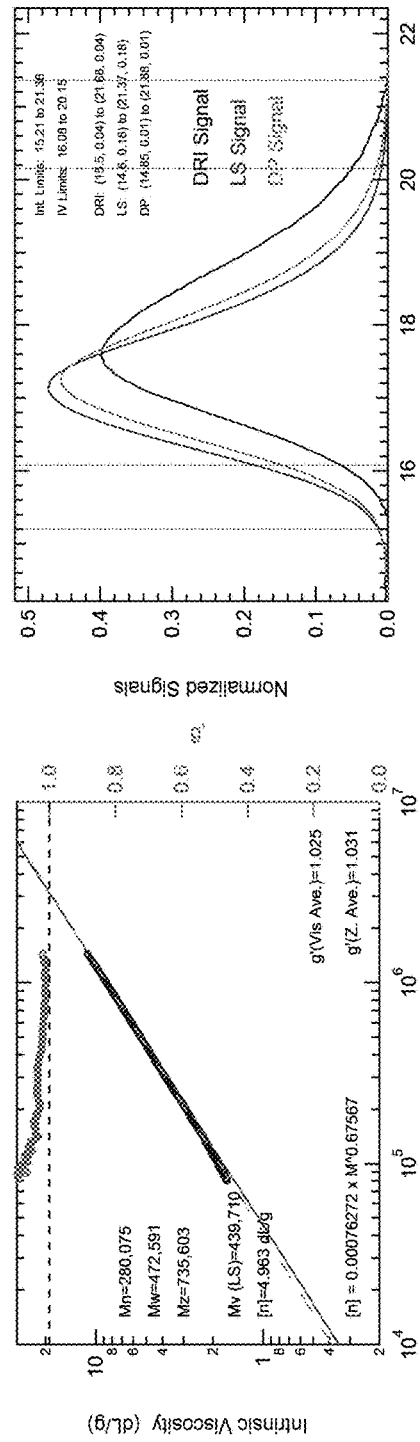
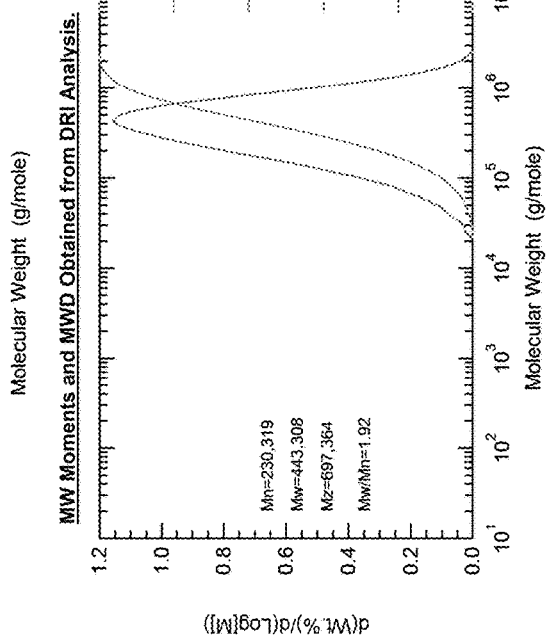

GPC data for Table 6, Entry 6 (catalyst = 1-Zr; polymer = EP)

FIGURE 13
GPC data for Table 6, Entry 12 (catalyst = 1-Hf; polymer = EP)
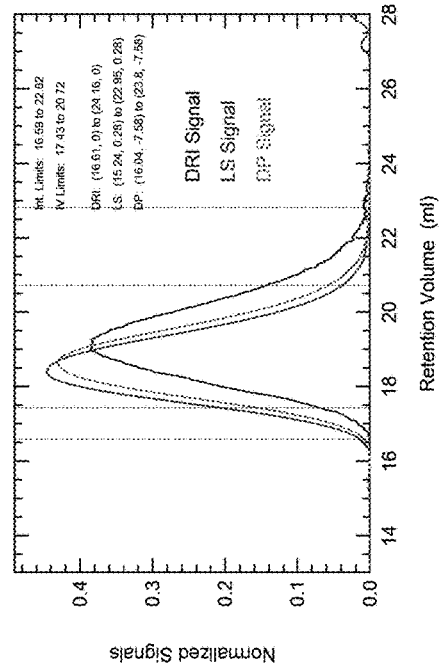
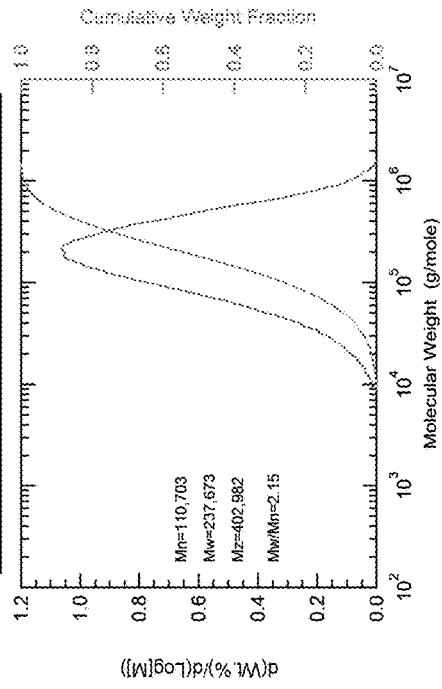
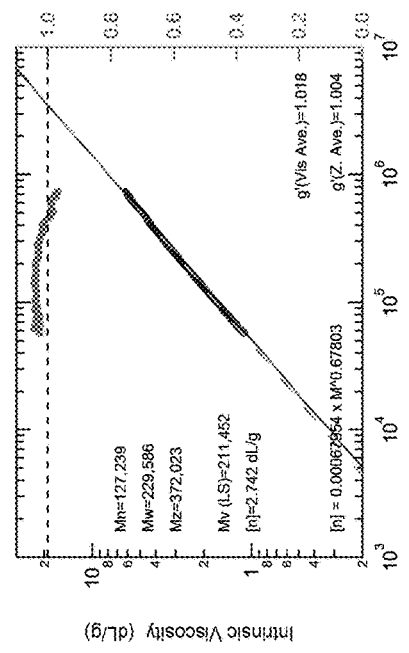

PHENOLATE TRANSITION METAL COMPLEXES, PRODUCTION AND USE THEREOF

PRIORITY CLAIM

This application claims priority to and the benefit of USSN 62/368,247, filed Jul. 29, 2016 and is incorporated by reference in its entirety.

FIELD OF THE INVENTION

The invention relates to phenolate ligands, phenolate transition metal complexes and processes for use of such complexes as catalysts for alkene polymerization processes, with or without chain transfer agents.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization have been based on bisphenolate complexes as catalyst precursors, which are typically activated with an alumoxane or with an activator containing a non-coordinating anion.

Diamine bis(phenolate) Group IV complexes have been used as transition metal components in the copolymerization of ethylene and hexene, see for example, Macromolecules 2005, 38, 2552-2558, and in the homopolymerization of 1-hexene, see for example J. Am. Chem. Soc. 2000, 122, 10706, and propylene, see for example, Macromolecules 2010, 43, 1689.

WO 2002/036638 and WO 2012/098521 disclose diamine bis(phenolate) compounds for use as alpha olefin polymerization catalysts.

WO 2012/027448 and WO 2003/091262 disclose bridged bis(phenyl phenol) compounds for olefin polymerization catalysts.

U.S. Pat. No. 8,071,701 discloses bridged polydentate catalyst complexes that produce low molecular weight (approx. 21,000 Mw or less) homopolypropylene where the examples have one carbon in the bridge.

Other references of interest include: WO 2016/003878; WO 2016/003879; U.S. Pat. Nos. 6,841,502; 6,596,827; WO 2014/143202; WO 2014/022746; WO 2014/022010; WO 2014/022012; WO 2014/22008; WO 2014/022011; WO 2015/088819; U.S. Pat. Nos. 8,791,2177, 812,104; 6,232,421; 6,333,389; 6,333,423; 8,907,032; WO 2007/130306; Israel Journal of Chemistry, Volume 42, 2002 pg. 373-381; Macromolecules, 2007, 40, 7061-7064; Chem. Comm. 2000, 379-380; Organometallics, 2001, 20, 3017-3028; Organometallics, 2005, 24, 200-202; Organometallics, 2009, 28, 1391-1405; Journal of Polymer Science, Part A: Polymer Chemistry, 2013, 51, 593-600; WO 2014/070502; US 2016/0280722; US 2017/0096509; Organometallics, 2002, 662-670; WO 2013/096573; Macromolecules 2013, 46, 2569-2575; J. Am. Chem. Soc., 2010, 132, 5566-5567; Macromolecules 2013, 46, 6758-6764; WO 2016/094861; WO 2016/089935; WO 2006/020624; US 2006/0025548; US 2006/0052554; WO 2005/108406; US 2006/0024517; U.S. Pat. Nos. 8,957,171; 8,957,172; 8,952,114; 9,045,568; 9,365,661; 9,382,349; 8,937,137; 9,150,676; 9,200,100; 9,200,099; 9,290,589; 9,534,070; US 2015/0291713; US 2015/0337062; US 2015/0344601; U.S. Pat. Nos. 9,000,108; 9,422,383; 8,609,794 and 9,193,813.

There still is need for adding to the range of catalysts complexes that may be prepared and broaden their performance in alkene polymerization. Further, there is a need in the art for new catalysts with high activity that can produce crystalline polymers with good molecular weights.

SUMMARY OF INVENTION

This invention relates to ligands represented by the formula (A):

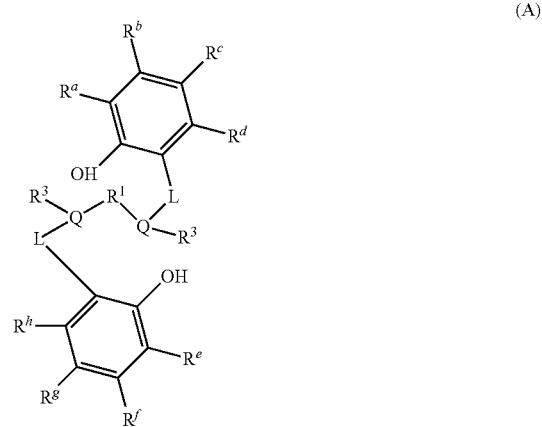

where each Q is a neutral group comprising at least one atom from Group 15 or Group 16 (such as O, N, S, or P), and $R^3$ is not present when Q is a Group 16 atom;
each L is independently

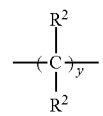

and is not part of an aromatic ring;
y is greater than or equal to 2;
$R^1$ is a divalent $C_1$-$C_{40}$ hydrocarbyl radical or divalent substituted hydrocarbyl radical comprising a portion that comprises a linker backbone comprising from 1 to 18 carbon atoms linking or bridging between the two Q groups;
each $R^a$, $R^b$, $R^c$, $R^d$, $R^e$, $R^f$, $R^g$, and $R^h$ is, independently, a hydrogen, a $C_1$-$C_{60}$ hydrocarbyl radical, a $C_1$-$C_{60}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;
each $R^2$ is independently a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic; and
each $R^3$ is independently a hydrogen, a $C_1$-$C_{40}$ hydrocarbyl radical, a $C_1$-$C_{40}$ substituted hydrocarbyl radical, a heteroatom or a heteroatom-containing group.

This invention relates to transition metal complexes represented by the formula (I):

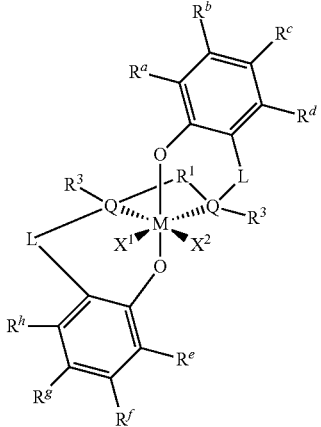

(I)

wherein M is a Group 4 transition metal;
each Q is neutral donor group comprising at least one atom from Group 15 or Group 16 (such as O, N, S, or P), and $R^3$ is not present when Q is a Group 16 atom;
each L is independently

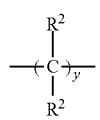

and is not part of an aromatic ring;
y is greater than or equal to 2;
$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic or heterocyclic structure;
$R^1$ is a divalent $C_1$-$C_{40}$ hydrocarbyl radical or divalent substituted hydrocarbyl radical comprising a portion that comprises a linker backbone comprising from 1 to 18 carbon atoms linking between the two Q groups;
each $R^a$, $R^b$, $R^c$, $R^d$, $R^e$, $R^f$, $R^g$, and $R^h$ is, independently, a hydrogen, a $C_1$-$C_{60}$ hydrocarbyl radical, a $C_1$-$C_{60}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;
each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic; and
each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group.

This invention relates to transition metal complexes represented by the formula (II)

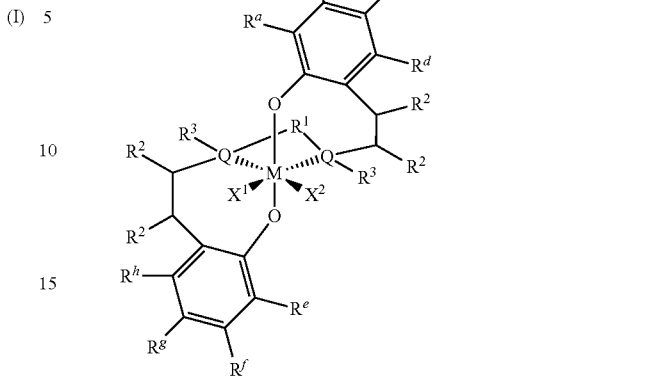

(II)

wherein M is a Group 4 transition metal;
each Q is neutral donor group comprising at least one atom from Group 15 or Group 16 (such as O, N, S, or P), and $R^3$ is not present when Q is a Group 16 atom;
$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic, or heterocyclic structure;
$R^1$ is a divalent $C_1$-$C_{40}$ hydrocarbyl radical or divalent substituted hydrocarbyl radical comprising a portion that comprises a linker backbone comprising from 1 to 18 carbon atoms linking or bridging between the two Q groups;
each $R^a$, $R^b$, $R^c$, $R^d$, $R^e$, $R^f$, $R^g$, and $R^h$ is, independently, a hydrogen, a $C_1$-$C_{60}$ hydrocarbyl radical, a $C_1$-$C_{60}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;
each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic, polycyclic or heterocyclic structure is not aromatic; and
each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group.

This invention also relates to a catalyst system comprising an activator and one or more catalysts compounds described herein.

This invention also relates to a process to make polyolefin using the catalyst systems described herein.

This invention further relates to methods to polymerize olefins using the above complex in the presence of a chain transfer agent.

BRIEF DESCRIPTION OF THE DRAWINGS

FIG. 10 is the GPC data for Table 1, Entry 25 (catalyst=1-Zr; polymer=HDPE).

FIG. 11 is the GPC data for Table 1, Entry 27 (catalyst=1-Hf; polymer=HDPE).

FIG. 13 is the GPC data for Table 6, Entry 12 (catalyst=1-Hf; polymer=EP).

DETAILED DESCRIPTION OF THE INVENTION

Figure 1:
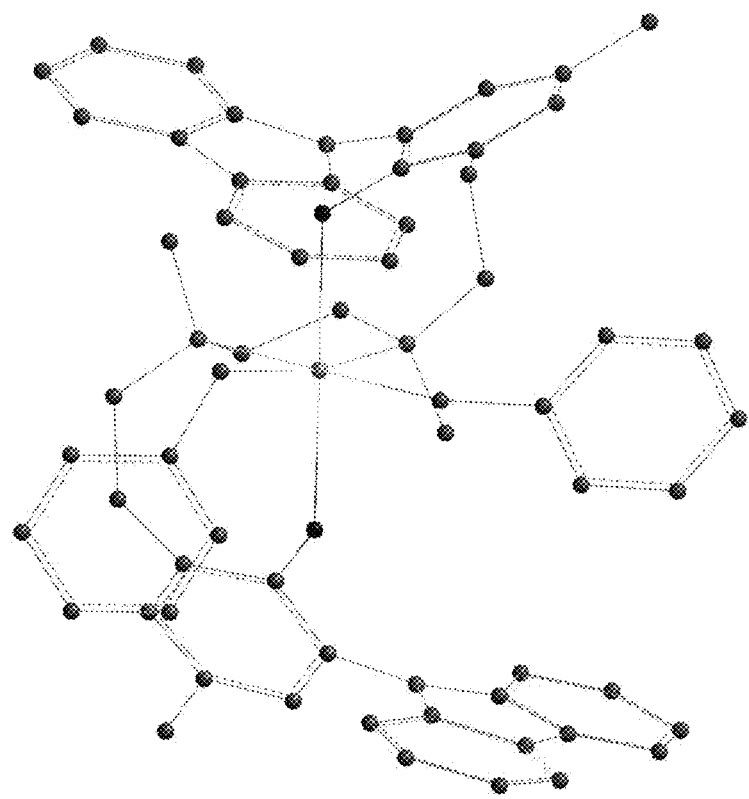
FIG. 1 is a representation of 1-Zr.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator, which is believed to create a cation as a result of the removal of an anionic group, often referred to as a leaving group, from the transition metal.

In the structures depicted throughout this specification and the claims, a solid line indicates a bond, an arrow indicates that the bond may be active, and each dashed line represents a bond having varying degrees of covalency and a varying degree of coordination.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and $^t$Bu are tertiary butyl, Pr is propyl, iPr and $^i$Pr are isopropyl, Cy is cyclohexyl, THF (also referred to as thf) is tetrahydrofuran, Bn is benzyl, $[H_2CO]_x$ is paraformaldehyde, and Ph is phenyl.

The terms "hydrocarbyl radical," "hydrocarbyl," and "hydrocarbyl group" are used interchangeably throughout this document unless otherwise specified. For purposes of this disclosure, a hydrocarbyl radical is defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic (including polycyclic) and aromatic or non-aromatic.

For purposes herein, a carbazole radical or substituted carbazole radical is represented by the formula:

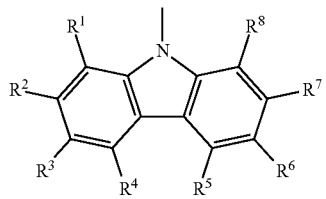

wherein each $R^1$ through $R^8$ is, independently, a hydrogen, a $C_1$-$C_{40}$ hydrocarbyl radical, a functional group comprising elements from Group 13 to 17 of the Periodic Table of the Elements, or two or more of $R^1$ to $R^8$ may independently join together to form a $C_4$ to $C_{62}$ cyclic or polycyclic ring structure, or a combination thereof.

A substituted or unsubstituted fluorenyl radical is represented by the formula:

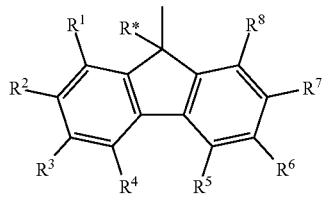

wherein each $R^1$ through $R^8$ is, independently, a hydrogen, a $C_1$-$C_{40}$ hydrocarbyl radical, a functional group comprising elements from Group 13 to 17 of the periodic table of the elements, or two or more of $R^1$ to $R^8$ may independently join together to form a $C_4$ to $C_{62}$ cyclic or polycyclic ring structure, or a combination thereof; R* is a hydrogen, a $C_1$-$C_{40}$ hydrocarbyl radical, a substituted $C_1$-$C_{40}$ hydrocarbyl radical (preferably R* is methyl, phenyl, or substituted phenyl).

The term "catalyst system" is defined to mean a complex/activator pair. When "catalyst system" is used to describe such a pair before activation, it means the unactivated catalyst complex (precatalyst) together with an activator, optionally, a chain transfer agent, and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably.

A "neutral donor group" is a neutrally charged group which donates one or more pairs of electrons to a metal.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered an α-olefin.

For purposes of this invention and claims thereto, the term "substituted" means that a hydrogen group has been replaced with a heteroatom, or a heteroatom-containing group. For example, a "substituted hydrocarbyl" is a radical made of carbon and hydrogen where at least one hydrogen is replaced by a heteroatom or heteroatom-containing group. However, for purposes of this invention and claims thereto in relation to the catalyst compounds described herein, the term "substituted" means that a hydrogen group has been replaced with a hydrocarbyl group, a heteroatom, or a heteroatom-containing group. For example, methyl cyclopentadiene (Cp) is a Cp group substituted with a methyl group.

Unless otherwise noted, all molecular weights units (e.g., Mw, Mn, Mz) are g/mol.

Unless otherwise noted all melting points ($T_m$) are DSC second melt.

The term "aryl", "aryl radical", and/or "aryl group" refers to aromatic cyclic structures, which may be substituted with hydrocarbyl radicals and/or functional groups as defined herein.

As used herein the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small portion of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

For purposes herein, RT is room temperature, which is defined as 25° C. unless otherwise specified. All percentages are weight percent (wt %) unless otherwise specified.

Catalyst Ligands and Compounds

In a first aspect, this invention relates to ligands represented by the formula (A):

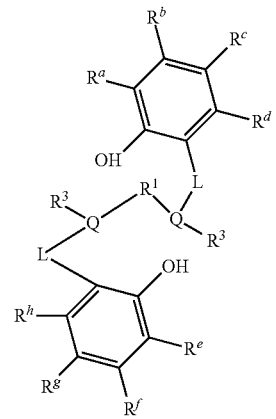

where each Q is neutral donor group comprising at least one atom from Group 15 or Group 16 (such as O, N, S, or P), and $R^3$ is not present when Q is a Group 16 atom;

each L is independently

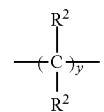

and is not part of an aromatic ring;

y is greater than or equal to 2, preferably 2, 3, 4, 5, or 6;

$R^1$ is a divalent $C_1$-$C_{40}$ (alternately $C_1$ to $C_{20}$) hydrocarbyl radical or divalent substituted hydrocarbyl radical comprising a portion that comprises a linker backbone comprising from 1 to 18 carbon atoms linking or bridging between the two Q groups, preferably as described below for formulas I and II;

each $R^a$, $R^b$, $R^c$, $R^d$, $R^e$, $R^f$, $R^g$, and $R^h$ is, independently, a hydrogen, a $C_1$-$C_{60}$ (alternately $C_1$ to $C_{40}$) hydrocarbyl radical, a $C_1$-$C_{60}$ (alternately $C_1$ to $C_{40}$) substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof, preferably as described below for formulas I and II;

each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic, preferably as described below for formulas I and II; and each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group, preferably as described below for formulas I and II.

In another aspect of the invention there is provided a transition metal complex (optionally for use in alkene polymerization) represented by the formula (I) or (II):

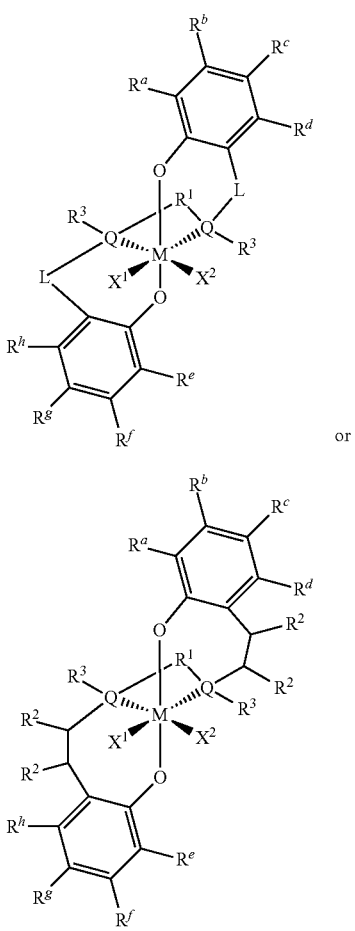

(I) or (II)

wherein M is a Group 4 transition metal (preferably Hf, Zr, or Ti, preferably Hf or Zr);
each L is independently

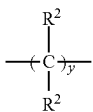

and is not part of an aromatic ring;
y is greater than or equal to 2, e.g., 2, 3, 4, 5, or 6;
$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic or heterocyclic ring structure (preferably benzyl, methyl, ethyl, chloro, bromo, and the like);
each Q is independently a neutral donor group comprising at least one atom from Group 15 or Group 16, preferably comprising O, N, S, or P (preferably O or N), and $R^3$ is not present when Q is a Group 16 atom;
$R^1$ is a divalent $C_1$-$C_{40}$ (alternately $C_1$ to $C_{20}$) hydrocarbyl radical or divalent substituted hydrocarbyl radical comprising a portion that comprises a linker backbone comprising from 1 to 18 carbon atoms linking or bridging between the two Q groups, preferably $R^1$ is a —$(CR^5_2)_n$— group, where n is 2, 3, 4, 5, or 6, (preferably 2 or 3) each $R^5$ is H or a $C_1$ to $C_{40}$ hydrocarbyl radical, a $C_1$ to $C_{40}$ substituted hydrocarbyl radical, a heteroatom or a heteroatom-containing group, or multiple $R^5$ groups may join together to form a $C_4$ to $C_{62}$ cyclic or polycyclic ring structure (preferably a benzene ring, substituted benzene ring, cyclohexyl, substituted cyclohexyl, cyclooctyl, or substituted cyclooctyl), preferably each $R^5$ is, independently, a $C_1$-$C_{20}$ hydrocarbyl radical, preferably a $C_1$-$C_{20}$ alkyl radical, preferably each $R^5$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl;

each $R^a$, $R^b$, $R^c$, $R^d$, $R^e$, $R^f$, $R^g$, and $R^h$ is, independently, a hydrogen, a $C_1$-$C_{60}$ (alternately $C_1$ to $C_{40}$) hydrocarbyl radical, a $C_1$-$C_{60}$ substituted hydrocarbyl radical, a heteroatom or a heteroatom-containing group, or two or more adjacent $R^a$ to $R^h$ groups may independently join together to form a $C_4$ to $C_{62}$ cyclic or polycyclic ring structure, or a combination thereof, preferably each $R^a$, $R^b$, $R^c$, $R^d$, $R^e$, $R^f$, $R^g$, and $R^h$ is, independently, a $C_1$-$C_{20}$ hydrocarbyl radical, preferably a $C_1$-$C_{20}$ alkyl or aromatic radical, preferably each $R^a$, $R^b$, $R^c$, $R^d$, $R^e$, $R^f$, $R^g$, and $R^h$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, adamantyl, substituted adamantyl, cyclohexyl, substituted cyclohexyl phenyl, substituted phenyl, fluorenyl, substituted fluorenyl, carbazolyl, substituted carbazolyl, naphthyl, substituted naphthyl, phenanthryl, substituted phenanthryl, anthracenyl, substituted anthracenyl, indanyl, substituted indanyl, indenyl, substituted indenyl;

each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic, preferably each $R^2$ is, independently, a $C_1$-$C_{20}$ hydrocarbyl radical, preferably a $C_1$-$C_{20}$ alkyl radical, preferably each $R^2$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl; and each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group, preferably a $C_1$-$C_{20}$ hydrocarbyl radical, preferably a $C_1$-$C_{20}$ alkyl radical, preferably each $R^3$ is, independently, selected from the group consisting of hydrogen, methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl, phenyl, and substituted phenyl.

In another aspect, this invention relates to catalyst compounds represented by the formula (I) or (II) where $R^a$ and/or $R^e$ (preferably $R^a$ and $R^e$) are independently a carbazole radical or substituted carbazole radical is represented by the formula:

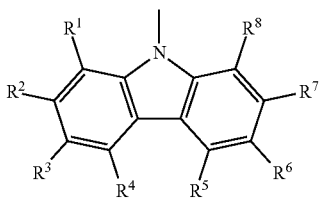

wherein each $R^1$, $R^2$, $R^3$, $R^4$, $R^5$, $R^6$, $R^7$, and $R^8$ is, independently, a hydrogen, a $C_1$-$C_{40}$ hydrocarbyl radical, a functional group comprising elements from Group 13 to 17 of the periodic table of the elements, or two or more of $R^1$ to $R^8$ may independently join together to form a $C_4$ to $C_{62}$ cyclic or polycyclic ring structure, or a combination thereof, preferably each $R^1$, $R^2$, $R^3$, $R^4$, $R^5$, $R^6$, $R^7$, and $R^8$ is hydrogen.

For purposes herein, any hydrocarbyl radical (and any alkyl radical) may be independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl.

In any embodiment of the transition metal complexes described herein M may be Hf, Ti or Zr.

In any embodiment of the transition metal complexes described herein, each of $X^1$ and $X^2$ is independently selected from the group consisting of hydrocarbyl radicals having from 1 to 20 carbon atoms (such as methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl), hydrides, amides, alkoxides having from 1 to 20 carbon atoms, sulfides, phosphides, halides, sulfoxides, sulfonates, phosphonates, nitrates, carboxylates, carbonates, and combinations thereof, preferably each of $X^1$ and $X^2$ is independently selected from the group consisting of halides (F, Cl, Br, I), alkyl radicals having from 1 to 7 carbon atoms (methyl, ethyl, propyl, butyl, pentyl, hexyl, heptyl, and isomers thereof), benzyl radicals, or a combination thereof.

In any embodiment of the transition metal complexes described herein, $R^1$ is a divalent $C_1$-$C_{40}$ hydrocarbyl radical or divalent substituted hydrocarbyl radical comprising a portion that comprises a linker backbone comprising from 1 to 18 carbon atoms linking or bridging between Q and Q. In an embodiment, $R^1$ is selected from the group consisting of ethylene (—$CH_2CH_2$—), 1,2-cyclohexylene and 1,2-phenylene. In an embodiment, $R^1$ is —$CH_2CH_2CH_2$-derived from propylene. In an embodiment, $R^1$ is selected form the group consisting of $C_1$ to $C_{20}$ alkyl groups, such as divalent methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl.

In a useful embodiment, each $R^a$, $R^b$, $R^c$, $R^d$, $R^e$, $R^f$, $R^g$, and $R^h$ is, independently, a hydrogen, a $C_1$-$C_{20}$ hydrocarbyl radical, a substituted $C_1$ to $C_{20}$ hydrocarbyl radical, or two or more of $R^1$ to $R^{10}$ may independently join together to form a $C_4$ to $C_{62}$ cyclic or polycyclic ring structure, or a combination thereof.

In any embodiment of the transition metal complexes described herein, each $R^a$, $R^b$, $R^c$, $R^d$, $R^e$, $R^f$, $R^g$, and $R^h$ is independently hydrogen, a halogen, a $C_1$ to $C_{30}$ hydrocarbyl radical, a $C_1$ to $C_{20}$ hydrocarbyl radical, or a $C_1$ to $C_{10}$ hydrocarbyl radical (such as methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl).

In any embodiment of the transition metal complexes described herein, each $R^a$, $R^b$, $R^c$, $R^d$, $R^e$, $R^f$, $R^g$, and $R^h$ is, independently, a substituted $C_1$ to $C_{30}$ hydrocarbyl radical, a substituted $C_1$ to $C_{20}$ hydrocarbyl radical, or a substituted $C_1$ to $C_{10}$ hydrocarbyl radical (such as 4-fluorophenyl, 4-chlorophenyl, 4-bromophenyl, 4-methoxyphenyl, 4-trifluoromethylphenyl, 4-dimethylaminophenyl, 4-trimethylsilylphenyl, 4-triethylsilylphenyl, trifluoromethyl, fluoromethyl, trichloromethyl, chloromethyl, mesityl, methylthio, phenylthio, (trimethylsilyl)methyl, and (triphenylsilyl)methyl).

In an embodiment of the invention, one or more of $R^a$, $R^b$, $R^c$, $R^d$, $R^e$, $R^f$, $R^g$, and $R^h$ is a methyl radical, a fluoride, chloride, bromide, iodide, methoxy, ethoxy, isopropoxy, trifluoromethyl, dimethylamino, diphenylamino, adamantyl, phenyl, pentafluorphenyl, naphthyl, anthracenyl, dimethylphosphanyl, diisopropylphosphanyl, diphenylphosphanyl, methylthio, and phenylthio or a combination thereof.

In any embodiment of the transition metal complexes described herein, Q is preferably a neutral donor group comprising at least one atom from Group 15 or Group 16, preferably Q is NR'$_2$, OR', SR', PR'$_2$, where R' is as defined for $R^a$ (preferably R' is methyl, ethyl, propyl, isopropyl, phenyl, cyclohexyl or linked together to form a five-membered ring such as pyrrolidinyl or a six-membered ring such as piperidinyl), preferably the -(-Q-$R^1$-Q-)- fragment can form a substituted or unsubstituted heterocycle which may or may not be aromatic and may have multiple fused rings. In any embodiment of the transition metal complexes described herein, Q is preferably NR'$_2$, where R' is methyl, ethyl, propyl, isopropyl, phenyl, cyclohexyl or linked together to form a five-membered ring such as pyrrolidinyl or a six-membered ring such as piperidinyl).

In a useful embodiment of the transition metal complexes described herein, $R^a$ and or $R^e$ are the same, preferably $R^a$ and or $R^e$ are C-'", where each R'" is H or a $C_1$ to $C_{12}$ hydrocarbyl or substituted hydrocarbyl (such as methyl, ethyl, ethenyl and isomers of propyl, butyl, pentyl, hexyl, heptyl, octyl, nonyl, decyl, undecyl, dodecyl, trifluoromethylphenyl, tolyl, phenyl, methoxyphenyl, tertbutylphenyl, fluorophenyl, diphenyl, dimethylaminophenyl, chlorophenyl, bromophenyl, iodophenyl, (trimethylsilyl)phenyl, (triethylsilyl)phenyl, (trimethylsilyl)methyl, (triethylsilyl) methyl). In a useful embodiment of the transition metal complexes described herein, $R^a$ and or $R^e$ are different.

In a useful embodiment of the transition metal complexes described herein, $R^a$ and or $R^e$ are the same, preferably $R^a$ and or $R^e$ are carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl. In a useful embodiment of the transition metal complexes described herein, $R^a$ and or $R^e$ are different. In a useful embodiment of the transition metal complexes described herein, $R^a$ and or $R^e$ are the same.

In an embodiment, M is Zr or Hf; $X^1$ and $X^2$ are benzyl radicals; and $R^1$ is ethylene (—CH$_2$CH$_2$—).

In an embodiment, M is Zr or Hf; $X^1$ and $X^2$ are benzyl radicals; $R^c$ and $R^g$ are methyl radicals; $R^b$, $R^d$, $R^h$, and $R^f$ are hydrogen; and $R^1$ is ethylene (—CH$_2$CH$_2$—), each Q is an O-containing group, $R^a$ and $R^e$ are carbazolyl or fluorenyl.

In a particularly preferred embodiment of the invention, the catalyst complex is represented by formula:

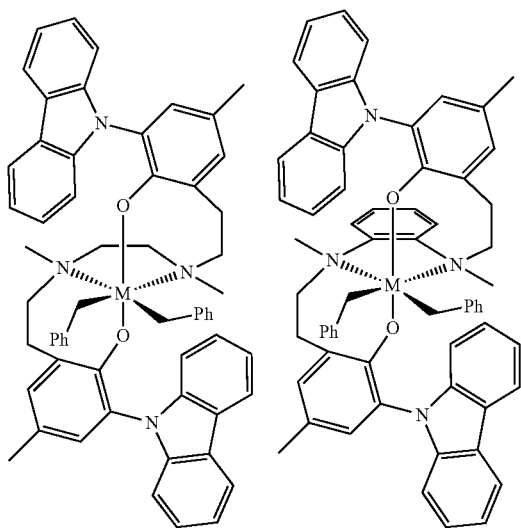

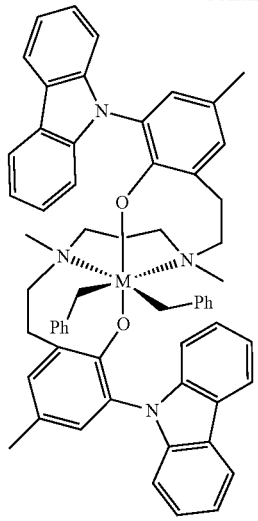

where M is preferably Zr or Hf.

Methods to Prepare the Catalyst Compounds

In embodiments, the transition metal compounds may be prepared by three general synthetic routes. In the first method, the phenol is allylated via a nucleophilic substitution followed by a Claisen rearrangement. The resulting allyl-substituted phenol is then protected and oxidized with ozone to the corresponding aldehyde. Reductive amination of the carbonyl with the diamine followed by deprotection results in the final ligand. Alternatively, the aldehyde can be transformed to the corresponding ethyl bromide compound, which is then reacted via nucleophilic substitution with the precursor of the bridging group, e.g., diamine or diol. In the second method, the phenol is ortho-formylated then transformed to the vinyl phenol via a Wittig reaction. The vinyl group is oxidized to the alcohol by hydroboration-oxidation then selectively transformed to the aldehyde, which is subsequently reacted as in Method 1 to the final ligand. In the third method, 2-(2-hydroxyphenyl)acetic acid is reduced to corresponding ethyl bromide following a reduction to the alcohol. The ethyl bromide compound is then protected and reacted as in Method 1. The ligand is then typically reacted with the metal tetra-alkyl compound, e.g., tetrabenzyl, to yield the metal dibenzyl complex of the ligand.

Method 1:

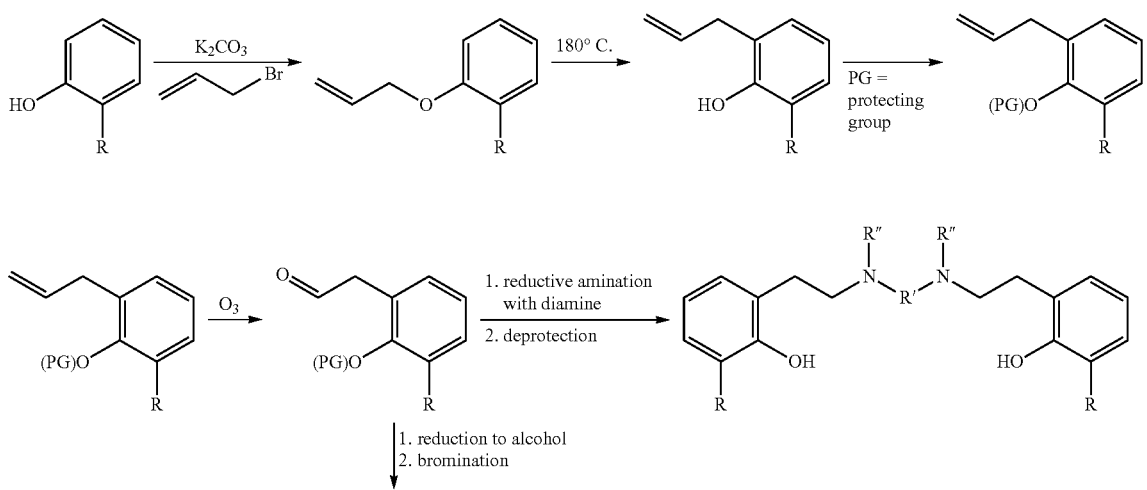

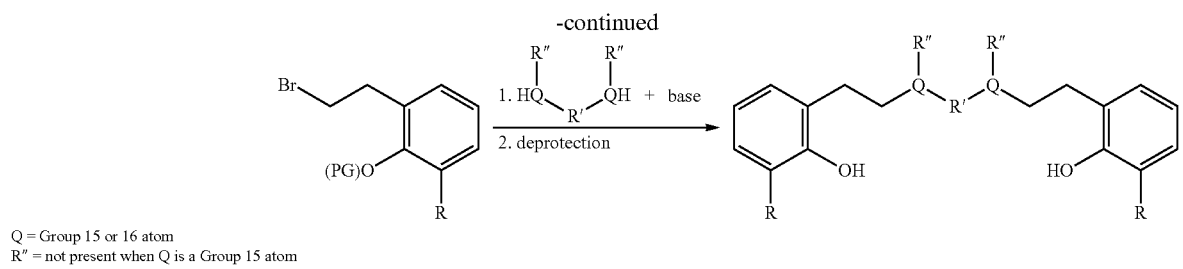

Q = Group 15 or 16 atom
R″ = not present when Q is a Group 15 atom

Method 2:

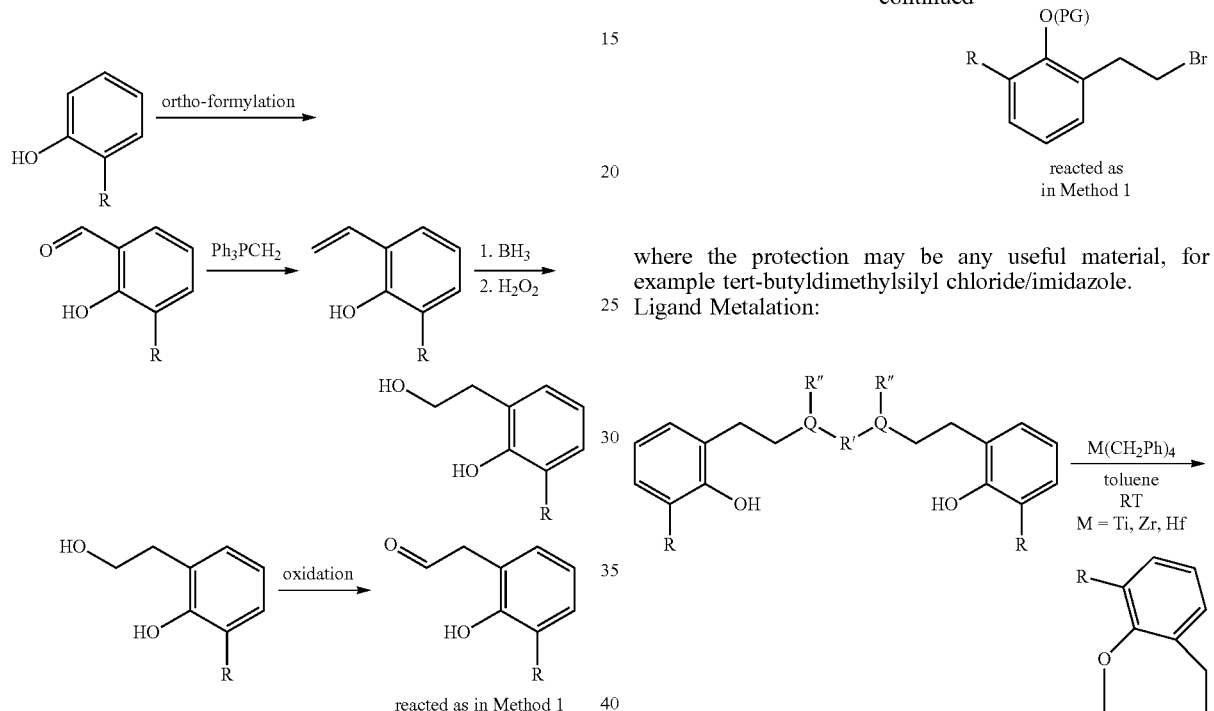

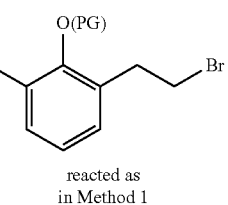

reacted as in Method 1 where the protection may be any useful material, for example tert-butyldimethylsilyl chloride/imidazole.

Ligand Metalation:

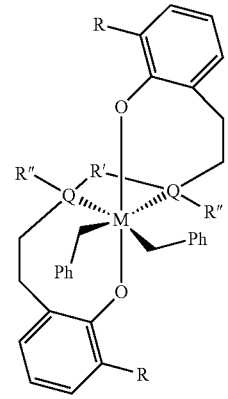

reacted as in Method 1

Method 3:

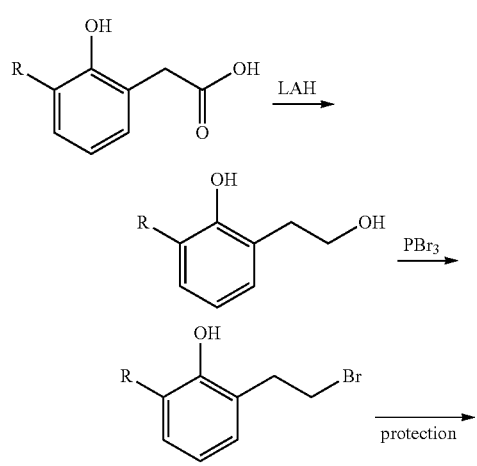

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion.

Non-limiting activators, for example, include alumoxanes, aluminum alkyls, ionizing activators, which may be neutral or ionic, and conventional-type cocatalyst. Preferred activators typically include alumoxane compounds, modified alumoxane compounds, and ionizing anion precursor compounds that abstract a reactive, σ-bound, metal ligand making the metal complex cationic and providing a charge-balancing non-coordinating or weakly coordinating anion.

Alumoxane Activators

In one embodiment, alumoxane activators are utilized as an activator in the catalyst system. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

Non-Coordinating Anion Activators

A non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment boron containing NCA activators represented by the formula below can be used:

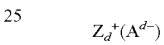

where: Z is (L-H) or a reducible Lewis acid; L is a neutral Lewis base; H is hydrogen;
(L-H) is a Brønsted acid; $A^{d-}$ is a boron containing non-coordinating anion having the charge d−; d is 1, 2, or 3.

The cation component, $Z_d^+$ may include Brønsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: ($Ar_3C^+$), where Ar is aryl or aryl substituted with a heteroatom, a $C_1$ to $C_{40}$ hydrocarbyl, or a substituted $C_1$ to $C_{40}$ hydrocarbyl), preferably the reducible Lewis acids in formula (14) above as "Z" include those represented by the formula: ($Ph_3C$), where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Brønsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ ($A^{d-}$) is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

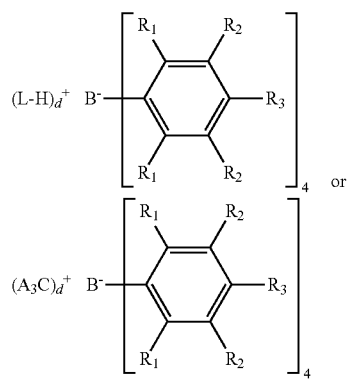

where:
each $R_1$ is, independently, a halide, preferably a fluoride;
Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group); each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);
L is a neutral Lewis base; (L-H)$^+$ is a Bronsted acid; d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3$V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$], 1-(4-(tris(pentafluorophenyl)borate)-2,3,5,6-tetrafluorophenyl)pyrrolidinium, and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, or triphenylcarbenium tetrakis(3,5-bis (trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl) phenyl)borate, di-(i-propyl)ammonium tetrakis(pentafluorophenyl)borate, (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1, alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see, for example, U.S. Pat. Nos. 5,153,157; 5,453,410; EP 0 573 120; WO 94/07928; and WO 95/14044, which discuss, inter alia, the use of an alumoxane in combination with an ionizing activator).

Scavengers and Co-Activators

The catalyst system may further include scavengers and/or co-activators. In some embodiments, when using the complexes described herein, particularly when they are immobilized on a support, the catalyst system will additionally comprise one or more scavenging compounds. Here, the term scavenging compound means a compound that removes polar impurities from the reaction environment. A scavenger is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

Typically, the scavenging compound will be an organometallic compound such as the Group-13 organometallic compounds of U.S. Pat. Nos. 5,153,157; 5,241,025; WO-A-91/09882; WO-A-94/03506; WO-A-93/14132; and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$). In an embodiment, the scavengers are present at less than 14 wt %, or from 0.1 to 10 wt %, or from 0.5 to 7 wt %, by weight of the catalyst system.

Suitable aluminum alkyl or organoaluminum compounds which may be utilized as co-activators include, for example, trimethylaluminum, triethylaluminum, triisobutylaluminum, tri-n-hexylaluminum, tri-n-octylaluminum and the like. In an embodiment, the co-activators are present at less than 14 wt %, or from 0.1 to 10 wt %, or from 0.5 to 7 wt %, by weight of the catalyst system. Alternately, the complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Chain Transfer Agents (CTAs)

A "chain transfer agent" is any agent capable of hydrocarbyl and/or polymeryl group exchange between a coordinative polymerization catalyst and the metal center of the chain transfer agent during a polymerization process. The chain transfer agent can be any desirable chemical compound such as those disclosed in WO 2007/130306. Preferably, the chain transfer agent is selected from Group 2, 12, or 13 alkyl or aryl compounds; preferably zinc, magnesium or aluminum alkyls or aryls; preferably where the alkyl is a $C_1$ to $C_{30}$ alkyl, alternately a $C_2$ to $C_{20}$ alkyl, alternately a $C_3$ to $C_{12}$ alkyl, typically selected independently from methyl, ethyl, propyl, butyl, isobutyl, tertbutyl, pentyl, hexyl, cyclohexyl, phenyl, octyl, nonyl, decyl, undecyl, and dodecyl; and where di-ethylzinc is particularly preferred.

In a particularly useful embodiment, this invention relates to a catalyst system comprising activator, catalyst complex as described herein, and chain transfer agent wherein the chain transfer agent is selected from Group 2, 12, or 13 alkyl or aryl compounds.

In a particularly useful embodiment, the chain transfer agent is selected from dialkyl zinc compounds, where the alkyl is selected independently from methyl, ethyl, propyl, butyl, isobutyl, tertbutyl, pentyl, hexyl, cyclohexyl, and phenyl.

In a particularly useful embodiment, the chain transfer agent is selected from trialkyl aluminum compounds, where the alkyl is selected independently from methyl, ethyl, propyl, butyl, isobutyl, tertbutyl, pentyl, hexyl, and cyclohexyl.

In a particularly useful embodiment, the chain transfer agent is selected from tri aryl aluminum compounds where the aryl is selected from phenyl and substituted phenyl.

The inventive process may be characterized by the transfer of at least 0.5 polymer chains (preferably 0.5 to 3) polymer chains, where n is the maximum number of polymer chains that can be transferred to the chain transfer agent metal, preferably n is 1 to 3 for trivalent metals (such as Al) and 1 to 2 for divalent metals (such as Zn), preferably n is 1.5 to 3 for trivalent metals (such as Al) and 1.5-2 for divalent metals (such as Zn). The number of chains transferred per metal is the slope of the plot of moles of polymer produced versus the moles of the chain transfer agent metal (as determined from at least four points, CTA metal:catalyst transition metal of 20:1, 80:1, 140:1 and 200:1, using least squares fit (Microsoft™ Excel 2010, version 14.0.7113.5000

(32 bit)) to draw the line. For example, in Table 10, for entries 1-8, the slope is 0.0682 and for entries 17-24, the slope is 0.7593.

Useful chain transfer agents are typically present at from 10 or 20 or 50 or 100 equivalents to 600 or 700 or 800 or 1000 or 2000 or 4000 equivalents relative to the catalyst component. Alternately the chain transfer agent is preset at a catalyst complex-to-CTA molar ratio of from about 1:12,000 to 10:1; alternatively 1:6,000; alternatively, 1:3,000 to 10:1; alternatively 1:2,000 to 10:1; alternatively 1:1,000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1.

Useful chain transfer agents include diethylzinc, tri-n-octyl aluminum, trimethylaluminum, triethylaluminum, tri-isobutylaluminum, tri-n-hexylaluminum, diethyl aluminum chloride, dibutyl zinc, di-n-propylzinc, di-n-hexylzinc, di-n-pentylzinc, di-n-decylzinc, di-n-dodecylzinc, di-n-tetradecylzinc, di-n-hexadecylzinc, di-n-octadecylzinc, diphenylzinc, diisobutylaluminum hydride, diethylaluminum hydride, di-n-octylaluminum hydride, dibutylmagnesium, diethylmagnesium, dihexylmagnesium, and triethylboron.

In a preferred embodiment, two or more complexes are combined with diethyl zinc and/or tri-n-octylaluminum in the same reactor with monomer(s). Alternately, one or more complexes is/are combined with another catalyst (such as a metallocene) and diethyl zinc and/or tri-n-octylaluminum in the same reactor with monomer(s).

In a preferred embodiment, one or more complexes is/are combined with a mixture of diethyl zinc and an aluminum reagent in the same reactor with monomer(s). Alternately, one or more complexes is/are combined with two chain transfer agents in the same reactor with monomer(s).

Supports

In some embodiments, the complexes described herein may be supported (with or without an activator) by any method effective to support other coordination catalyst systems, effectively meaning that the catalyst so prepared can be used for oligomerizing or polymerizing olefin in a heterogeneous process. The catalyst precursor, activator, co-activator, if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100 to 200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 µm is suitable for use in this invention. Various embodiments select a porous support material, such as for example, talc, inorganic oxides, inorganic chlorides, for example, magnesium chloride and resinous support materials such as polystyrene polyolefin or polymeric compounds or any other organic support material and the like. Some embodiments select inorganic oxide materials as the support material including Group -2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can, optionally, double as the activator component, however, an additional activator may also be used.

The support material may be pretreated by any number of methods. For example, inorganic oxides may be calcined, chemically treated with dehydroxylating agents, such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 µm. Some embodiments select a surface area of 50-500 $m^2/g$, a pore volume of 0.5-3.5 cc/g, or an average particle size of 10-200 µm. Other embodiments select a surface area of 100-400 $m^2/g$, a pore volume of 0.8-3.0 cc/g, and an average particle size of 50-100 µm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Inventive catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry-in-liquid diluent, or gas phase-in-gaseous diluent). In the case of heterogeneous slurry or gas phase polymerization, the complex and activator may be supported. Silica is useful as a support herein. Chain transfer agents may also be used herein.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and, optionally, also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1, 3,5,5-trimethylhexene-1, and 5-ethylnonene-1.

In some embodiments, the monomer mixture may also comprise one or more dienes at up to 10 wt %, such as from 0.00001 to 1.0 wt %, for example, from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene ("ENB"), 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

In a useful embodiment of the invention, the monomers comprise ethylene and one or more $C_3$ to $C_{12}$ alkenes, such as propylene.

Particularly preferred monomers combinations include: ethylene-propylene, ethylene-hexene, ethylene-octene, and the like.

Where olefins are used that give rise to short chain branching, such as propylene, the catalyst systems may, under appropriate conditions, generate stereoregular polymers or polymers having stereoregular sequences in the polymer chains.

Polymer Products

The homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %. In some embodiments herein, a multimodal polyolefin composition is produced, comprising a first polyolefin component and at least another polyolefin component, different from the first polyolefin component by molecular weight, preferably such that the GPC trace has more than one peak or inflection point.

Unless otherwise indicated, measurements of weight average molecular weight (Mw), number average molecular weight (Mn), and z average molecular weight (Mz) are determined by the GPC-SEC procedure as described below in the Experimental section.

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC-SEC.

In an alternate embodiment, the homopolymer and copolymer products produced by the present process may have a multi-modal, such as bimodal, Mw/Mn.

The term "multimodal," when used to describe a polymer or polymer composition, means "multimodal molecular weight distribution," which is understood to mean that the Gel Permeation Chromatography (GPC-SEC) trace, plotted as Absorbance versus Retention Time (seconds), has more than one peak or inflection point. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition.

In an alternate embodiment, the polymer produced herein has an Mw/Mn of from 1 to 40, alternately from greater than 1 to 5.

End Uses

Articles made using polymers produced herein may include, for example, molded articles (such as containers and bottles, e.g., household containers, industrial chemical containers, personal care bottles, medical containers, fuel tanks, and storage ware, toys, sheets, pipes, tubing) films, non-wovens, and the like. It should be appreciated that the list of applications above is merely exemplary, and is not intended to be limiting.

EXPERIMENTAL

[H$_2$CO]$_x$ is paraformaldehyde.

Example 1

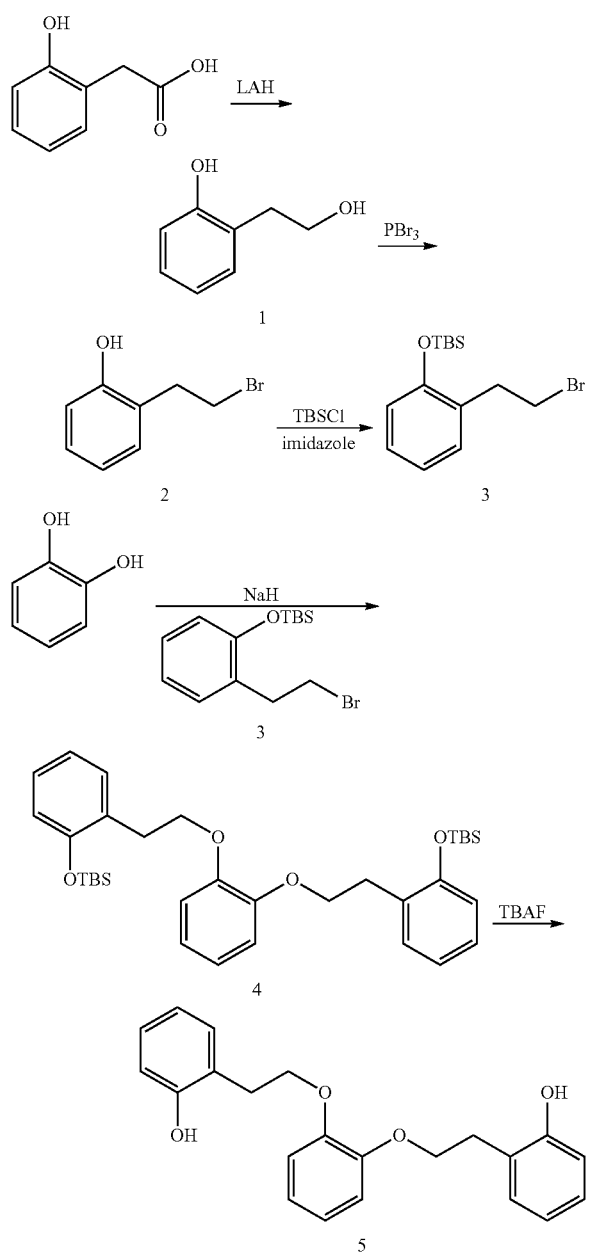

2-(2-hydroxyethyl)phenol (1): 2-(2-hydroxyphenyl)acetic acid (5.0 g, 32 mmol) was dissolved in 160 mL of THF and cooled to −35° C. Borane (49 mL of 1.0 M in THF) was slowly added and the reaction warmed to ambient temperature. After 4 h, the mixture was cooled to 0° C. and quenched with concentrated HCl. Once warmed to ambient, saturated ammonium chloride was added and THF removed by distillation under reduced pressure. The aqueous portion was extracted with ethyl acetate, which was then dried over MgSO$_4$, filtered, and concentrated to give the reduced alcohol in quantitative yield. $^1$H NMR (400 MHz, CDCl$_3$, δ): 2.19 (t, J=8.0 Hz, 2 H), 4.01 (t, J=8.0 Hz, 2H), 6.92 (m, 4 H).

2-(2-bromoethyl)phenol (2): Alcohol 1 (2.0 g, 14.4 mmol) was dissolved in 30 mL of dichloromethane and cooled to −35° C. Phosphorous tribromide (2.0 mL, 21.7 mmol) was slowly added and the reaction warmed to ambient temperature over several hours. The reaction was poured onto ice and extracted with methylene chloride. The combined organic layers were washed with saturated sodium bicarbonate, dried over MgSO$_4$, filtered, and concentrated to give the product as a pale yellow oil in 62% yield. $^1$H NMR (400 MHz, CDCl$_3$, δ).

(2-(2-bromoethyl)phenoxy)(tert-butyl)dimethylsilane (3): Bromide 2 (1.8 g, 8.9 mmol), imidazole (2.2 g, 23.9 mmol), and tert-butyldimethylsilyl chloride (1.4 g, 9.79 mmol) were dissolved in 30 mL of acetonitrile and stirred at ambient temperature for over 24 h. Water was added and the mixture extracted with 2 portions of ethyl acetate. Combined organic layers were washed with brine, dried over MgSO$_4$, filtered through a silica gel plug, and then concentrated to give a protected phenol. $^1$H NMR (400 MHz, CDCl$_3$, δ): 0.26 (s, 6 H), 1.03 (s, 9 H), 3.17 (t, J=8.0 Hz, 2 H), 3.54 (t, J=8.0 Hz, 2 H), 6.87 (m, 2 H), 7.11 (m, 2 H).

1,2-bis(2-((tert-butyldimethylsilyl)oxy)phenethoxy)benzene (4): Catechol (104 mg, 0.95 mmol) was dissolved in 15 mL of THF and cooled to 0° C. Sodium hydride (101 mg, 3.99 mmol) was added and the mixture allowed to warm to ambient temperature and stirred for 30 min. The catecholate salt was added to a solution of bromide 3 (0.6 g, 1.9 mmol) in 5 mL of THF and stirred for 5 h. The reaction was quenched with ice water and extracted with ether. Combined organic layers were washed with brine, dried over MgSO$_4$, filtered, and concentrated under reduced pressure to give the product as a pale yellow oil.

Example A

Synthesis of 1-Zr and 1-Hf

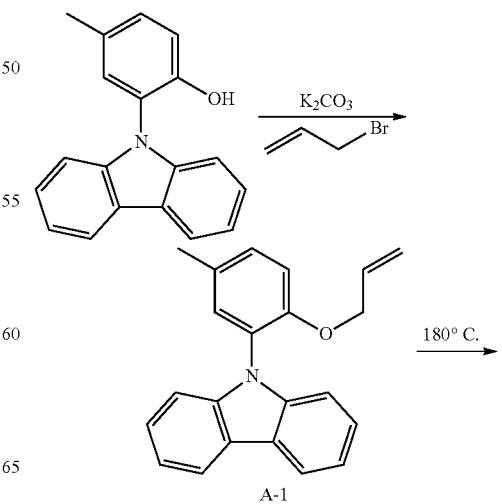

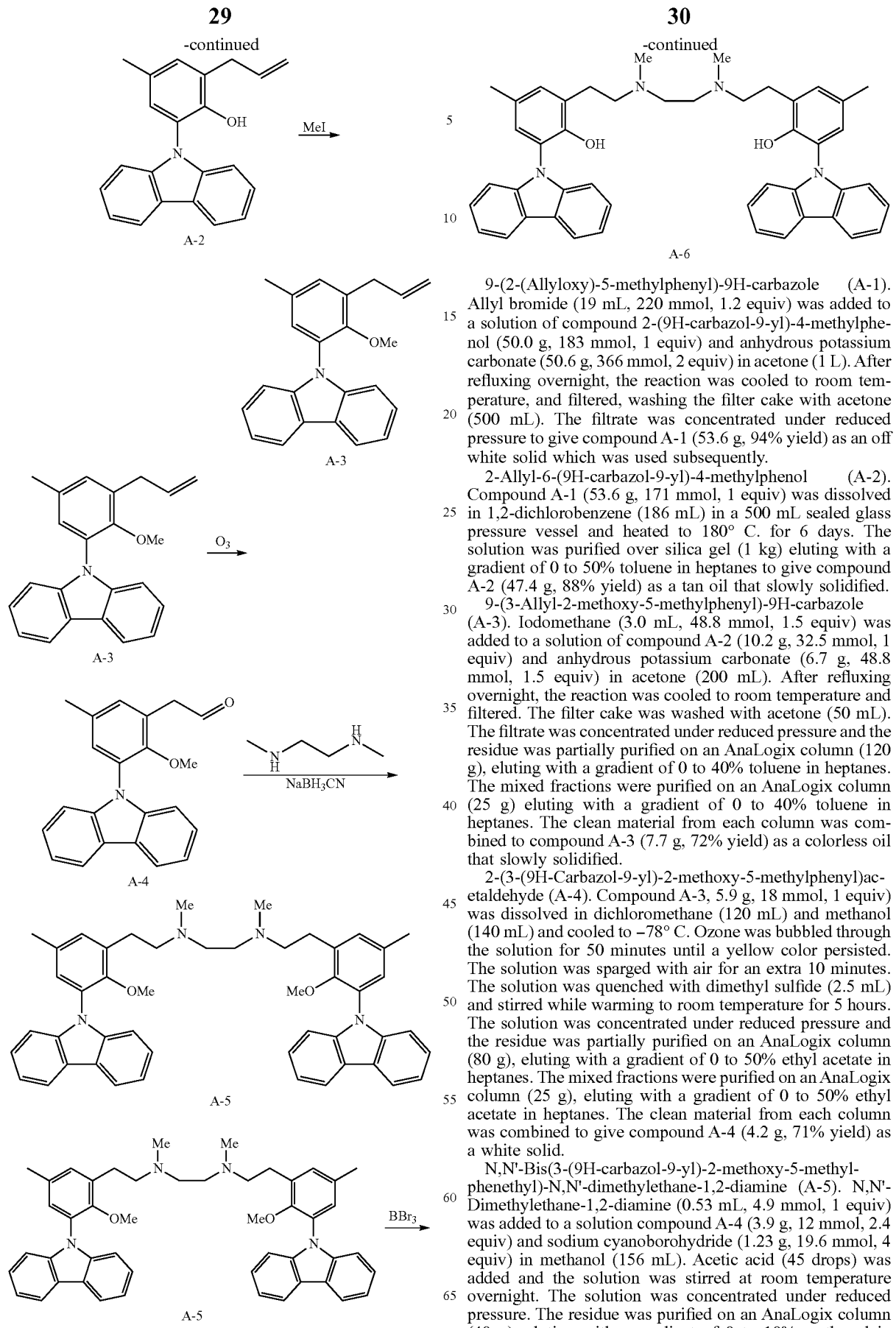

9-(2-(Allyloxy)-5-methylphenyl)-9H-carbazole (A-1). Allyl bromide (19 mL, 220 mmol, 1.2 equiv) was added to a solution of compound 2-(9H-carbazol-9-yl)-4-methylphenol (50.0 g, 183 mmol, 1 equiv) and anhydrous potassium carbonate (50.6 g, 366 mmol, 2 equiv) in acetone (1 L). After refluxing overnight, the reaction was cooled to room temperature, and filtered, washing the filter cake with acetone (500 mL). The filtrate was concentrated under reduced pressure to give compound A-1 (53.6 g, 94% yield) as an off white solid which was used subsequently.

2-Allyl-6-(9H-carbazol-9-yl)-4-methylphenol (A-2). Compound A-1 (53.6 g, 171 mmol, 1 equiv) was dissolved in 1,2-dichlorobenzene (186 mL) in a 500 mL sealed glass pressure vessel and heated to 180° C. for 6 days. The solution was purified over silica gel (1 kg) eluting with a gradient of 0 to 50% toluene in heptanes to give compound A-2 (47.4 g, 88% yield) as a tan oil that slowly solidified.

9-(3-Allyl-2-methoxy-5-methylphenyl)-9H-carbazole (A-3). Iodomethane (3.0 mL, 48.8 mmol, 1.5 equiv) was added to a solution of compound A-2 (10.2 g, 32.5 mmol, 1 equiv) and anhydrous potassium carbonate (6.7 g, 48.8 mmol, 1.5 equiv) in acetone (200 mL). After refluxing overnight, the reaction was cooled to room temperature and filtered. The filter cake was washed with acetone (50 mL). The filtrate was concentrated under reduced pressure and the residue was partially purified on an AnaLogix column (120 g), eluting with a gradient of 0 to 40% toluene in heptanes. The mixed fractions were purified on an AnaLogix column (25 g) eluting with a gradient of 0 to 40% toluene in heptanes. The clean material from each column was combined to compound A-3 (7.7 g, 72% yield) as a colorless oil that slowly solidified.

2-(3-(9H-Carbazol-9-yl)-2-methoxy-5-methylphenyl)acetaldehyde (A-4). Compound A-3, 5.9 g, 18 mmol, 1 equiv) was dissolved in dichloromethane (120 mL) and methanol (140 mL) and cooled to −78° C. Ozone was bubbled through the solution for 50 minutes until a yellow color persisted. The solution was sparged with air for an extra 10 minutes. The solution was quenched with dimethyl sulfide (2.5 mL) and stirred while warming to room temperature for 5 hours. The solution was concentrated under reduced pressure and the residue was partially purified on an AnaLogix column (80 g), eluting with a gradient of 0 to 50% ethyl acetate in heptanes. The mixed fractions were purified on an AnaLogix column (25 g), eluting with a gradient of 0 to 50% ethyl acetate in heptanes. The clean material from each column was combined to give compound A-4 (4.2 g, 71% yield) as a white solid.

N,N'-Bis(3-(9H-carbazol-9-yl)-2-methoxy-5-methylphenethyl)-N,N'-dimethylethane-1,2-diamine (A-5). N,N'-Dimethylethane-1,2-diamine (0.53 mL, 4.9 mmol, 1 equiv) was added to a solution compound A-4 (3.9 g, 12 mmol, 2.4 equiv) and sodium cyanoborohydride (1.23 g, 19.6 mmol, 4 equiv) in methanol (156 mL). Acetic acid (45 drops) was added and the solution was stirred at room temperature overnight. The solution was concentrated under reduced pressure. The residue was purified on an AnaLogix column (40 g), eluting with a gradient of 0 to 10% methanol in dichloromethane, to give compound A-5 (3.7 g, >theoretical yield) as a colorless oil that slowly solidified.

6,6'-((Ethane-1,2-diylbis(methylazanediyl))bis(ethane-2,1-diyl))bis(2-(9H-carbazol-9-yl)-4-methylphenol) (A-6). Boron tribromide (3.0 mL, 31 mmol, 6.4 equiv) as added dropwise to solution of compound A-5 (3.5 g, 4.9 mmol, 1 equiv) in anhydrous dichloromethane (100 mL) at −78° C. The solution was stirred at −78° C. for 4 hours and warmed to room temperature overnight. The solution was carefully diluted with ice water (100 mL). The layers were separated and the aqueous layer was extracted with dichloromethane (100 mL). The combined organic layers were dried over sodium sulfate and concentrated under reduced pressure. The crude reside was dry loaded onto silica (8 g) and partially purified on an AnaLogix column (40 g), eluting with a gradient of 0 to 100% ethyl acetate in heptanes. The mixed fractions from the first column were partially purified on an AnaLogix column (40 g), eluting with a gradient of 0 to 100% methyl tert-butyl ether in heptanes. The mixed fractions from the second column were partially purified in batches, two runs on an AnaLogix Reverse Phase column (100 g) and seven runs on an AnaLogix Reverse Phase column (50 g), eluting each batch with a gradient of 0 to 100% tetrahydrofuran in deionized water. The mixed fractions from the reverse phase columns were partially purified on an AnaLogix column (12 g) eluting isocratically with a solution of 98:2:1 dichloromethane:methyl tert-butyl ether:ammonia. The mixed fractions were partially purified on an AnaLogix column (25 g), eluting isocratically with a solution of 98:2:1 dichloromethane:methyl tert-butyl ether:ammonia. The mixed fractions were purified one last time on an AnaLogix column (12 g), eluting isocratically with a solution of 98:2:1 dichloromethane:methyl tert-butylether:ammonia. All of the clean material was combined to give compound A-6 (1.42 g, 42% yield) as a white solid.

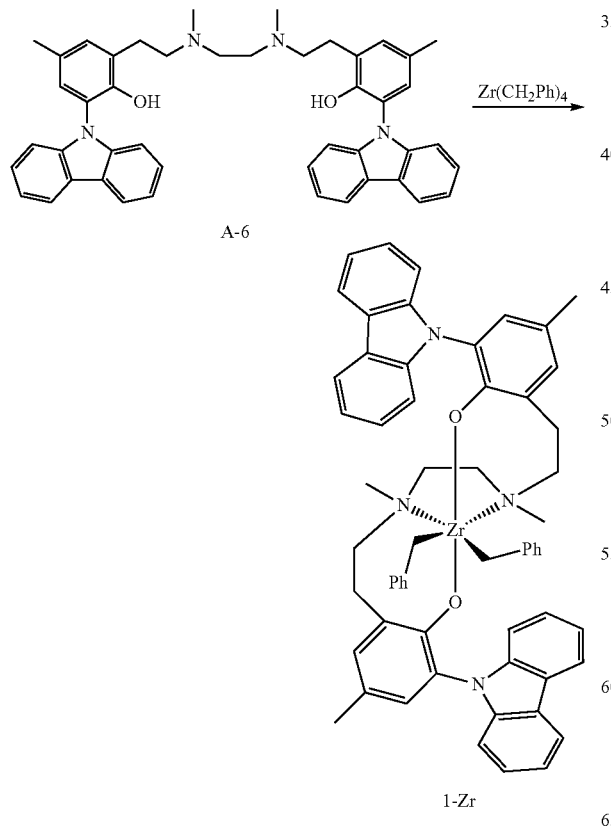

6,6'-((Ethane-1,2-diylbis(methylazanediyl))bis(ethane-2,1-diyl))bis(2-(9H-carbazol-9-yl)-4-methylphenoxide) zirconium dibenzyl (1-Zr). In the drybox, Zr(CH$_2$Ph)$_4$ (0.0996 g, 0.219 mmol, 1 equiv) was dissolved in toluene (3 mL), and the resulting orange solution was added to a slurry of compound A-6 (0.1500 g, 0.2184 mmol, 1 equiv) in toluene (2 mL). The mixture was stirred for 2.5 hours at room temperature then concentrated under a stream of nitrogen. The resulting yellow-orange residue was washed with hexane (5 mL) and dried under vacuum to give 1-Zr (0.1836 g, ~88% yield) as a yellow powder.

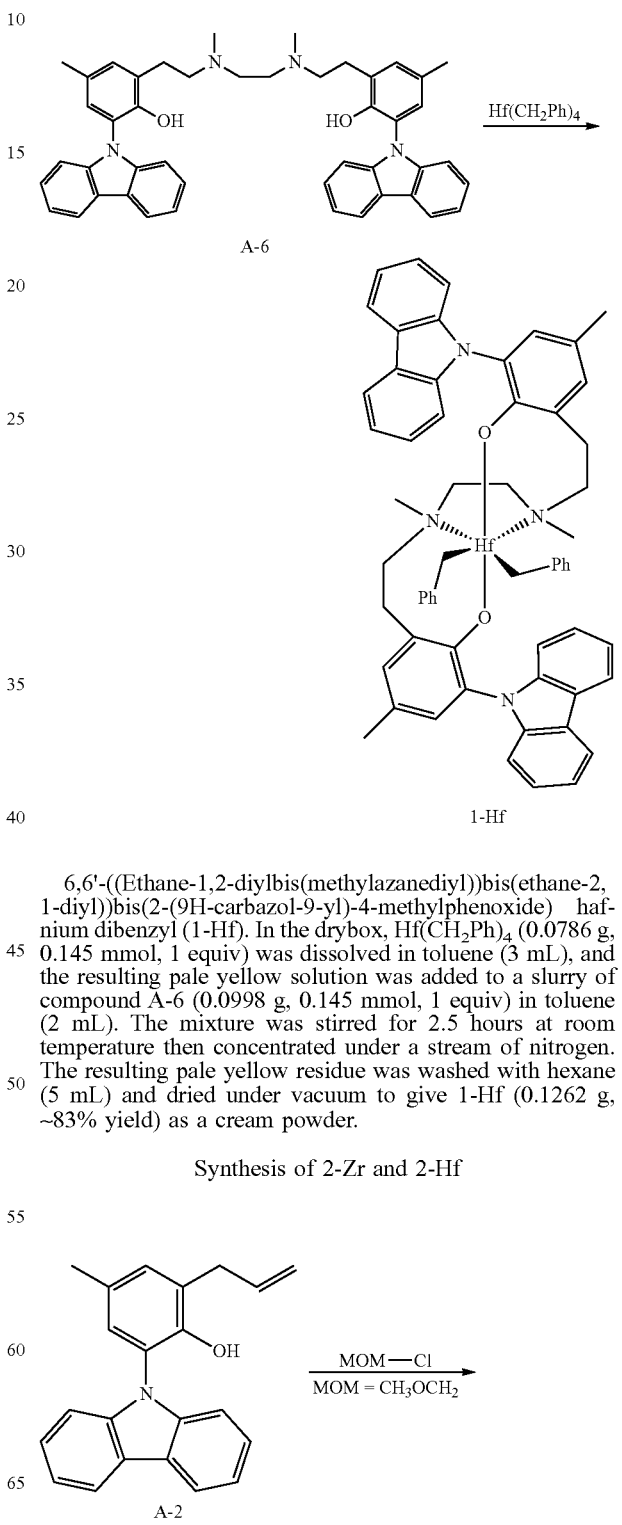

6,6'-((Ethane-1,2-diylbis(methylazanediyl))bis(ethane-2,1-diyl))bis(2-(9H-carbazol-9-yl)-4-methylphenoxide) hafnium dibenzyl (1-Hf). In the drybox, Hf(CH$_2$Ph)$_4$ (0.0786 g, 0.145 mmol, 1 equiv) was dissolved in toluene (3 mL), and the resulting pale yellow solution was added to a slurry of compound A-6 (0.0998 g, 0.145 mmol, 1 equiv) in toluene (2 mL). The mixture was stirred for 2.5 hours at room temperature then concentrated under a stream of nitrogen. The resulting pale yellow residue was washed with hexane (5 mL) and dried under vacuum to give 1-Hf (0.1262 g, ~83% yield) as a cream powder.

Synthesis of 2-Zr and 2-Hf

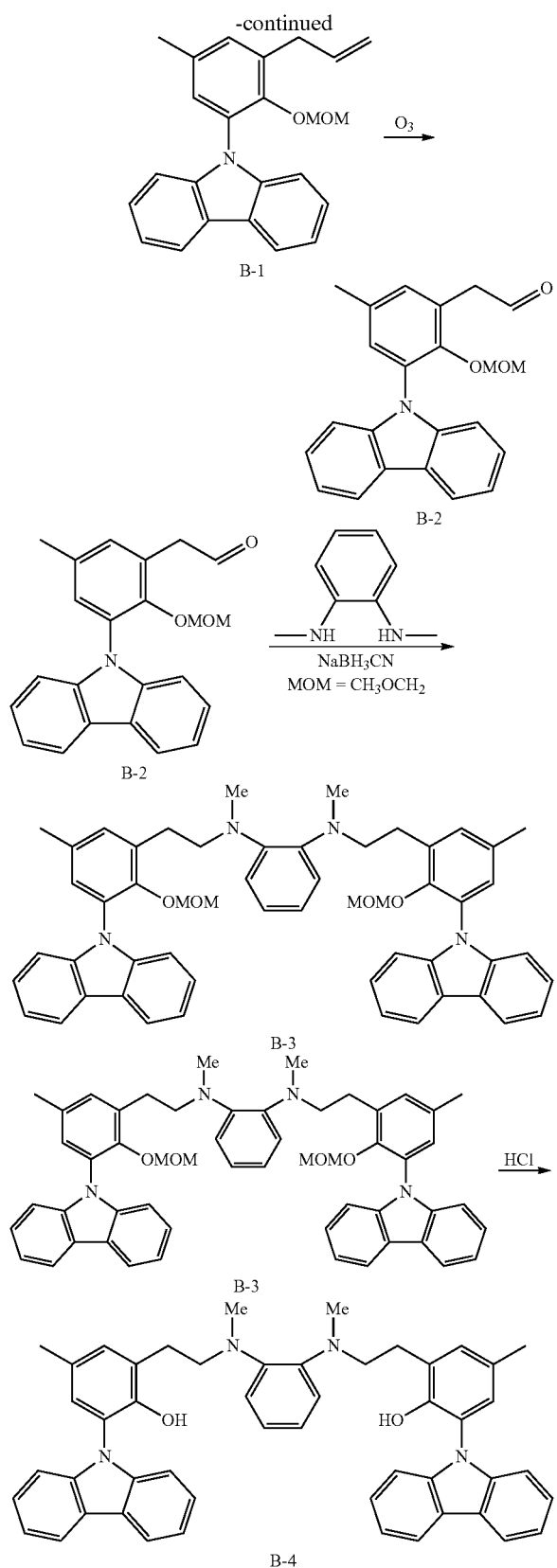

mmol, 2 equiv) and N,N-diisopropylethylamine (50.6 mL, 290 mmol, 2 equiv) were dissolved in dichloromethane (450 mL) and refluxed for 6.5 hours. The solution was diluted with water (400 mL) and the layers were separated. The aqueous layer was extracted with dichloromethane (100 mL). The combined organic layers were concentrated under reduced pressure. The residue was partially purified over silica gel (1 kg), eluting with a gradient of 10 to 50% toluene in heptanes. The mixed fractions from the first column were purified on an AnaLogix column (330 g), eluting with a gradient of 10 to 50% toluene in heptanes. The clean material from each column was combined to give compound B-1 (41.7 g, 73% yield) as a yellow oil.

2-(3-(9H-Carbazol-9-yl)-2-(methoxymethoxy)-5-methylphenyl)acetaldehyde (B-2). Compound B-1 (30.7 g, 85.9 mmol, 1 equiv) was dissolved in dichloro-methane (600 mL) and methanol (700 mL) and cooled to −78° C. Ozone was bubbled through the solution for 2.5 hours until a yellow color persisted. The solution was sparged with air for an additional 10 minutes. The solution was quenched with dimethyl sulfide (12 mL) and stirred while warming to room temperature for 5 hours. The solution was concentrated under reduced pressure. The residue was purified over silica gel (300 g), eluting with a gradient of 0 to 60% ethyl acetate in heptanes, to give compound B-2 (20.5 g, 66% yield) as a yellow oil.

N,N'-Bis(3-(9H-carbazol-9-yl)-2-(methoxymethoxy)-5-methylphenethyl)-N,N'-dimethylbenzene-1,2-diamine (B-3): Sodium cyanoborohydride (1.8 g, 29.2 mmol, 4 equiv) and acetic acid (3.6 mL, 57 mmol, 7.8 equiv) were added to a solution of compound B-2 (6.3 g, 17.6 mmol, 2.4 equiv) and N,N'-dimethylbenzene-1,2-diamine (1.0 g, 7.3 mmol, 1 equiv) in methanol (250 mL). The solution was stirred at room temperature overnight. The solution was filtered and the filtrate was partially concentrated under reduced pressure and filtered again. The solids from each filtration were combined, dissolved in dichloromethane and dry loaded onto Celite (10 g). The dry loaded solid was then partially purified on an AnaLogix column (120 g), eluting with a gradient of 0 to 25% ethyl acetate in heptanes. The mixed fractions from the first column were combined and dry loaded onto Celite (5 g) and partially purified on an AnaLogix column (80 g), eluting with a gradient of 0 to 25% ethyl acetate in heptanes. The mixed fractions from the second column were combined and dry loaded onto Celite (5 g) and partially purified on an AnaLogix column (80 g), eluting with a gradient of 0 to 25% ethyl acetate in heptanes. The clean material from each column was combined to give compound B-3 (2.5 g, 42% yield) as a white solid.

6,6'-((1,2-Phenylenebis(methylazanediyl))bis(ethane-2,1-diyl))bis(2-(9H-carbazol-9-yl)-4-methylphenol) (B-4). Compound B-4 (2.4 g, 3.3 mmol, 1 equiv) was dissolved in a solution of 2.5% v/v concentrated hydrochloric acid in methanol (102.5 mL) and stirred at 45° C. for 5 hours. Solid sodium bicarbonate (6.5 g) was added to neutralize the solution to pH 8. The solution was concentrated under reduced pressure. The residue was partitioned between ethyl acetate (200 mL) and water (200 mL). The organic layer was dried over sodium sulfate and concentrated under reduced pressure. The residue was dry loaded onto Celite (5 g) and purified on an AnaLogix column (25 g), eluting with a 9-(3-Allyl-2-(methoxymethoxy)-5-methylphenyl)-9H-carbazole (B-1). Compound A-2 (45.4 g, 145 mmol, 1 equiv), chloromethyl methyl ether (MOM-Cl, 22 mL, 290 gradient of 0 to 25% ethyl acetate in heptanes, to give compound B-4 (1.5 g, 71% yield) as a white solid.

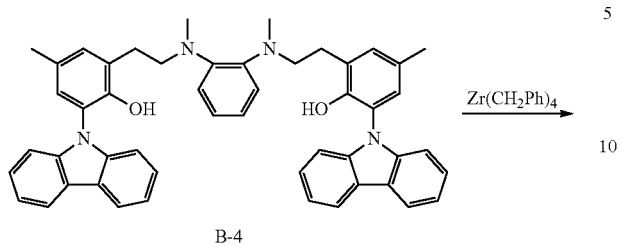

B-4

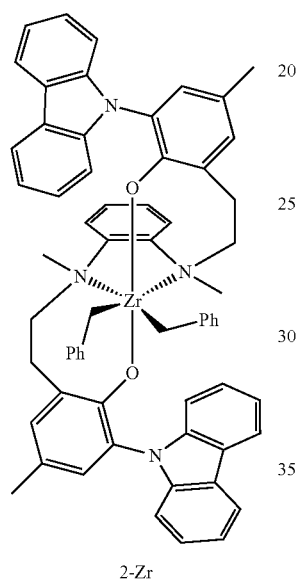

2-Zr 6,6'-((1,2-phenylenebis(methylazanediyl))bis(ethane-2,1-diyl))bis(2-(9H-carbazol-9-yl)-4-methylphenoxide) zirconium dibenzyl (2-Zr). In the drybox, Zr(CH$_2$Ph)$_4$ (0.0606 g, 0.133 mmol, 1 equiv) was dissolved in toluene (3 mL), and the resulting orange solution was added to a solution of compound B-4 (0.0998 g, 0.136 mmol, 1 equiv) in toluene (2 mL). The mixture was stirred for 2.5 hours at room temperature then concentrated under a stream of nitrogen. The resulting yellow-orange residue was stirred in hexane (5 mL), collected in a funnel with a glass frit and dried under vacuum to give 2-Zr (0.0983 g, ~73% yield) as a yellow powder.

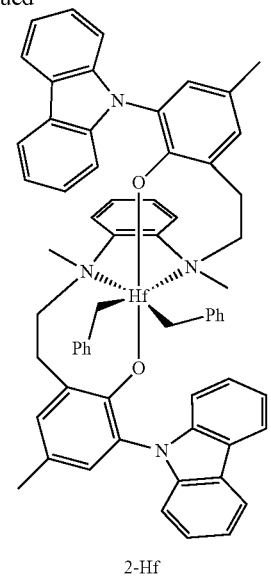

2-Hf 6,6'-((1,2-phenylenebis(methylazanediyl))bis(ethane-2,1-diyl))bis(2-(9H-carbazol-9-yl)-4-methylphenoxide) hafnium dibenzyl (2-Hf). In the drybox, Hf(CH$_2$Ph)$_4$ (0.0726 g, 0.134 mmol, 1 equiv) was dissolved in toluene (3 mL), and the resulting pale yellow solution was added to a solution of compound B-4 (0.0992 g, 0.135 mmol, 1 equiv) in toluene (2 mL). The mixture was stirred for 2.5 hours at room temperature then concentrated under a stream of nitrogen. The resulting pale yellow residue was washed with hexane (5 mL) and dried under vacuum to give 2-Hf (0.1180 g, ~81% yield) as a cream powder.

Synthesis of 3-Zr and 3-Hf

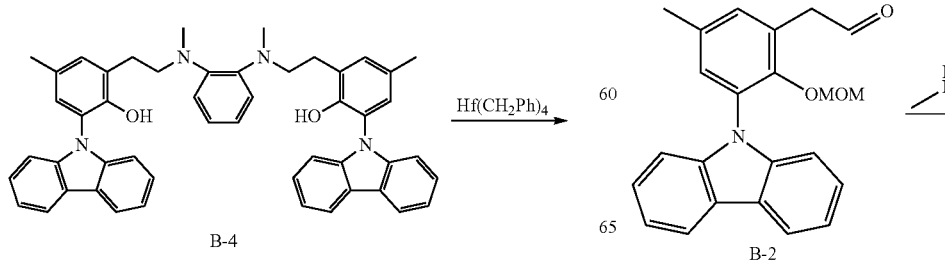

B-4

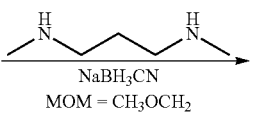

B-2

-continued

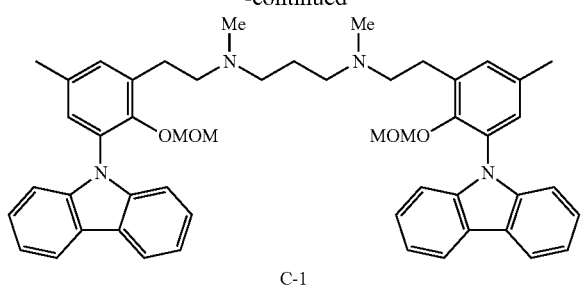

C-1

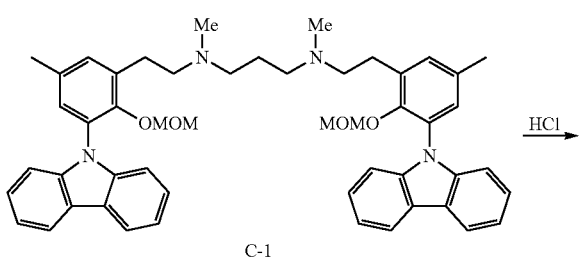

C-1

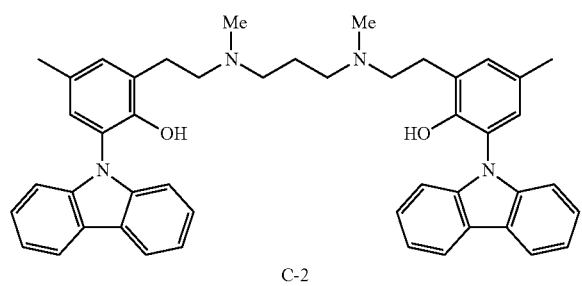

C-2

N,N'-bis(3-(9H-carbazol-9-yl)-2-(methoxymethoxy)-5-methylphenethyl)-N,N'-dimethylpropane-1,3-diamine (C-1). Sodium cyanoborohydride (0.556 g, 8.85 mmol, 4 equiv) and acetic acid (10 drops) were added to a solution of compound B-2 (1.904 g, 5.30 mmol, 2.4 equiv) and N,N'-dimethylpropane-1,3-diamine (0.226 g, 2.21 mmol, 1 equiv) in methanol (25 mL). The solution was stirred at room temperature overnight then filtered and concentrated under reduced pressure. The resulting residue was purified on a Biotage SNAP Ultra column (50 g), eluting with a gradient of 0 to 20% ethyl acetate in hexane, to give compound C-1 as an off-white solid. The compound was carried over to the next step as isolated.

6,6'-(2,2'-(propane-1,3-diylbis(methylazanediyl))bis(ethane-2,1-diyl))bis(2-(9H-carbazol-9-yl)-4-methylphenol) (C-2). Compound C-1 (from previous reaction) was dissolved in 30 mL of methanol and a solution of 2.5% v/v concentrated hydrochloric acid in methanol (10.3 mL) and stirred at 45° C. for 5 hours. Solid sodium bicarbonate was added to neutralize the solution to pH 8. The solution was concentrated under reduced pressure. The residue was partitioned between ethyl acetate (50 mL) and water (50 mL). Organic layer washed with water (2×50 mL) and brine (1×50 mL). The organic layer was separated, dried over sodium sulfate, and concentrated under reduced pressure. The resulting residue was purified on a Biotage SNAP Ultra column (50 g), eluting with a gradient of 0 to 20% ethyl acetate in hexane, to give compound C-2 (0.954 g, 62% overall yield) as a white solid.

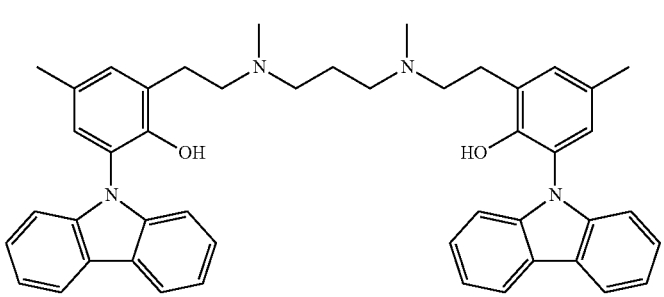

C-2

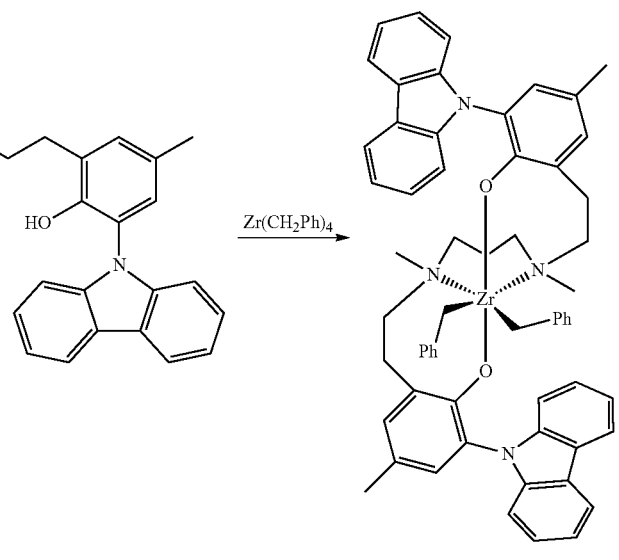

3-Zr 6,6'-(2,2'-(propane-1,3-diylbis(methylazanediyl))bis(ethane-2,1-diyl))bis(2-(9H-carbazol-9-yl)-4-methylphenoxide) zirconium dibenzyl (3-Zr). In the drybox, Zr(CH$_2$Ph)$_4$ (0.099 g, 0.217 mmol, 1 equiv) was dissolved in toluene (3 mL), and the resulting orange solution was added to a solution of compound C-2 (0.152 g, 0.217 mmol, 1 equiv) in toluene (2 mL). The mixture was stirred for 1 hour at room temperature then concentrated under a stream of nitrogen. The resulting yellow-orange residue was stirred in hexane (10 mL), collected in a funnel with a glass frit and dried under vacuum to give 3-Zr (0.169 g, 80% yield) as a yellow powder.

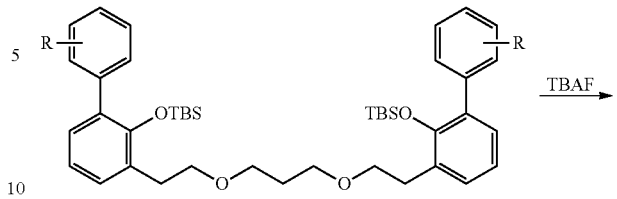

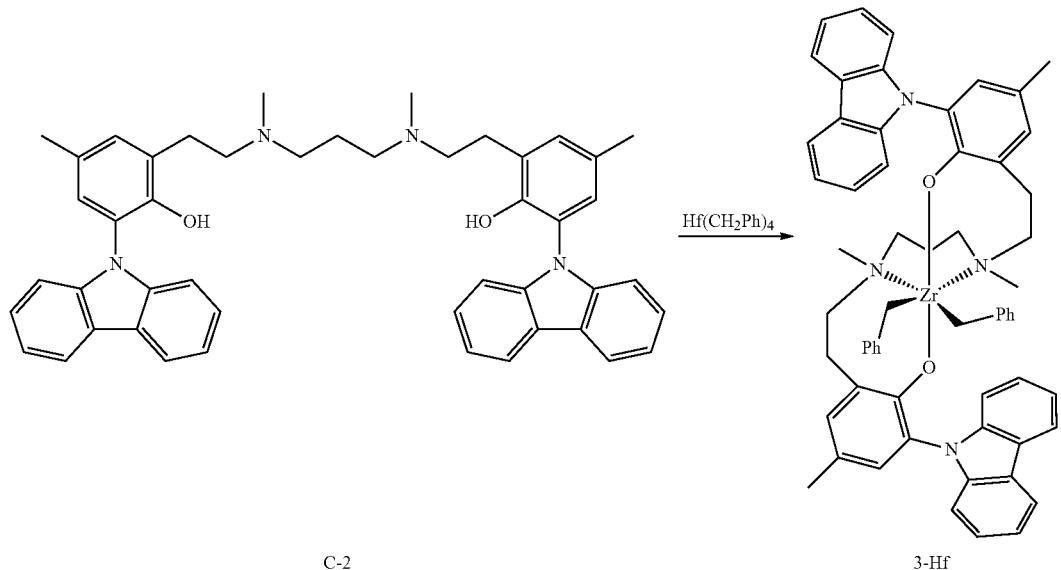

6,6'-(2,2'-(propane-1,3-diylbis(methylazanediyl))bis(ethane-2,1-diyl))bis(2-(9H-carbazol-9-yl)-4-methylphenoxide) hafnium dibenzyl (3-Hf). In the drybox, Hf(CH$_2$Ph)$_4$ (0.136 g, 0.250 mmol, 1 equiv) was dissolved in toluene (3 mL), and the resulting pale yellow solution was added to a solution of compound C-2 (0.175 g, 0.250 mmol, 1 equiv) in toluene (2 mL). The mixture was stirred for 1 hour at room temperature then concentrated under a stream of nitrogen. The resulting off-white residue was stirred in hexane (10 mL), collected in a funnel with a glass frit, washed with hexane, and dried under vacuum to give 3-Hf (0.213 g, 80% yield) as a white powder.

Likewise, the following can also be made:

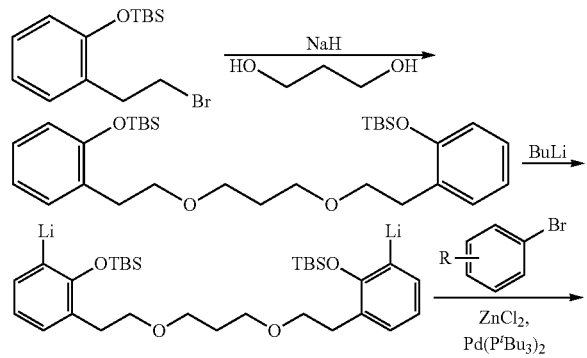

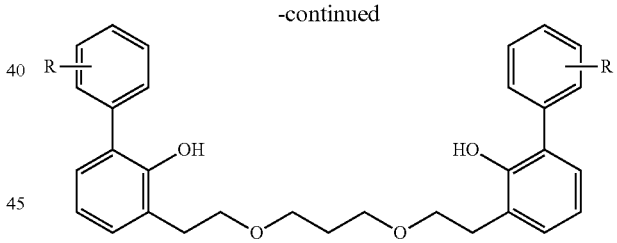

Preparation of Supported Catalysts

Preparation of Silica Support (sMAO). MAO (71.4 g, 30 wt % toluene solution, 351.1 mmol of Al) was slowly added to a slurry of silica (D948, 40.7 g, calcined at 600° C.) in toluene (200 mL). The slurry was heated to 80° C., stirred for 1 hour then filtered and washed with toluene (3×70 mL) and pentane (70 mL). The silica support was dried under vacuum overnight to give a free flowing white solid (60.7 g).

Preparation of Supported Catalyst. In the drybox, a slurry of sMAO (0.500 g) in toluene (30 mL) was prepared in a Cel-Stir reaction vessel. The slurry was charged with a toluene (3 mL) solution of the metal complex (0.020 mmol), and the reaction was stirred at room temperature for 1 hour. The slurry was filtered through a funnel with a glass frit (10 micron), washed with toluene (5 mL) and pentane (10 mL), and dried under vacuum for 1 hour to afford a free flowing yellow or white solid (~0.5 g; catalyst loading=0.040 mmol metal complex/g sMAO). In the following polymerization examples, supported catalysts are indicated by "_s" following the catalyst name. For example, catalyst 1-Zr supported on silica is labeled as 1-Zr s.

Polymerization Examples

General Polymerization Procedures for Parallel Pressure Reactor. Solvents, polymerization-grade toluene, and isohexane were supplied by ExxonMobil Chemical Company and purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company).

1-octene (C8) and 1-hexene (C6) (98%, Aldrich Chemical Company) were dried by stirring over NaK overnight followed by filtration through basic alumina (Aldrich Chemical Company, Brockman Basic 1).

Polymerization-grade ethylene (C2) was used and further purified by passing the gas through a series of columns: 500 cc Oxyclear cylinder from Labclear (Oakland, Calif.) followed by a 500 cc column packed with dried 3 Å mole sieves (8-12 mesh; Aldrich Chemical Company) and a 500 cc column packed with dried 5 Å mole sieves (8-12 mesh; Aldrich Chemical Company).

Polymerization grade propylene (C3) was used and further purified by passing it through a series of columns: 2250 cc Oxiclear cylinder from Labclear followed by a 2250 cc column packed with 3 Å mole sieves (8-12 mesh; Aldrich Chemical Company), then two 500 cc columns in series packed with 5 Å mole sieves (8-12 mesh; Aldrich Chemical Company), then a 500 cc column packed with Selexsorb CD (BASF), and finally a 500 cc column packed with Selexsorb COS (BASF).

Solutions of the metal complexes and activators were prepared in a drybox using toluene (ExxonMobil Chemical Company; anhydrous, stored under nitrogen; 98%). Concentrations were typically 0.2 mmol/L for the metal complexes and N,N-dimethyl anilinium tetrakis-pentafluorophenyl borate (Activator-1) and 0.5% w/w for methyl alumoxane (MAO).

Slurries of supported catalysts in toluene were prepared in the drybox using 45 mg of the supported catalyst and 15 mL of toluene. The resulting mixture was vortexed for uniform distribution of particles prior to injection.

For polymerization experiments with supported catalysts or Activator-1 as activator, tri-n-octylaluminum (TNOAL, neat, AkzoNobel) was used as a scavenger. Concentration of the TNOAL solution in toluene ranged from 0.5 to 2.0 mmol/L.

Polymerizations were carried out in a parallel, pressure reactor, as generally described in U.S. Pat. Nos. 6,306,658; 6,455,316; 6,489,168; WO 00/09255; and Murphy et al., J. Am. Chem. Soc., 2003, 125, pp. 4306-4317, each of which is fully incorporated herein by reference. The experiments were conducted in an inert atmosphere ($N_2$) drybox using autoclaves equipped with an external heater for temperature control, glass inserts (internal volume of reactor=23.5 mL for C2 and C2/C8; 22.5 mL for C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours. Although the specific quantities, temperatures, solvents, reactants, reactant ratios, pressures, and other variables are frequently changed from one polymerization run to the next, the following describes a typical polymerization performed in a parallel, pressure reactor.

Catalyst systems dissolved in solution were used in the polymerization examples below, unless specified otherwise.

Ethylene Homopolymerization (HDPE) and Ethylene-Octene Copolymerization (EO). A pre-weighed glass vial insert and disposable stirring paddle were fitted to each reaction vessel of the reactor, which contains 48 individual reaction vessels. The reactor was then closed and purged with ethylene. Each vessel was charged with enough solvent (typically isohexane) to bring the total reaction volume, including the subsequent additions, to the desired volume, typically 5 mL. 1-octene, if required, was injected into the reaction vessel and the reactor was heated to the set temperature and pressurized to the predetermined pressure of ethylene, while stirring at 800 rpm. The aluminum and/or zinc compound in toluene was then injected as scavenger and/or chain transfer agent followed by addition of the activator solution (typically 1.0-1.2 molar equivalents of N,N-dimethyl anilinium tetrakis-pentafluorophenyl borate—Activator-1).

The catalyst solution (typically 0.020-0.080 umol of metal complex) was injected into the reaction vessel and the polymerization was allowed to proceed until a pre-determined amount of ethylene (quench value typically 20 psi) had been used up by the reaction. Alternatively, the reaction may be allowed to proceed for a set amount of time (maximum reaction time typically 30 minutes). Ethylene was added continuously (through the use of computer controlled solenoid valves) to the autoclaves during polymerization to maintain reactor gauge pressure (+/−2 psig) and the reactor temperature was monitored and typically maintained within +/−1° C. The reaction was quenched by pressurizing the vessel with compressed air. After the reactor was vented and cooled, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent octene incorporation, and by DSC (see below) to determine melting point (Tm).

For polymerizations using MAO as activator (typically 100 to 1000 molar equivalents), the MAO solution was injected into the reaction vessel after the addition of 1-octene and prior to heating the vessel to the set temperature and pressurizing with ethylene. No additional aluminum reagent was used as scavenger during these runs.

Equivalence is determined based on the mole equivalents relative to the moles of the transition metal in the catalyst complex.

Ethylene-Propylene Copolymerization (EP). The reactor was prepared as described above and purged with propylene. Isohexane was then injected into each vessel at room temperature followed by a predetermined amount of propylene gas. The reactor was heated to the set temperature and pressurized with the required amount of ethylene while stirring at 800 rpm. The scavenger, activator (typically Activator-1) and catalyst solutions were injected sequentially to each vessel and the polymerization was allowed to proceed as described previously.

Propylene Homopolymerization (PP). The reactor was prepared as described above and purged with propylene.

Isohexane was then injected into each vessel at room temperature followed by a predetermined amount of propylene gas. The reactor was heated to the set temperature while stirring at 800 rpm, and the scavenger, activator (typically Activator-1) and catalyst solutions were injected sequentially to each vessel. The polymerization was allowed to proceed as described previously.

For propylene homopolymerization in the presence of hydrogen ($PP/H_2$), the reactor was prepared as described above and purged with 25% v/v $H_2/N_2$ gas. With an atmosphere of $H_2/N_2$ gas in the reaction vessel, isohexane, the scavenger solution and a predetermined amount of propylene gas were injected sequentially at room temperature. The reactor was then heated to the set temperature followed by sequential injection of the activator and catalyst solutions. The polymerization was allowed to proceed as described previously.

For polymerizations using MAO as activator, the MAO solution was injected into the vessel after the addition of isohexane. No additional aluminum reagent was used as scavenger during these runs.

Polymerizations Using Supported Catalysts. For ethylene-hexene copolymerization (EH), the reactor was prepared as described above and purged with ethylene. Isohexane, 1-hexene, and the scavenger solution were added sequentially to the reaction vessel via syringe at room temperature and atmospheric pressure. The reactor was then heated to the process temperature (85° C.) and charged with ethylene to the pressure setpoint (130 psig=896 kPa) while stirring at 800 rpm. The supported catalyst slurry was injected into the vessel and the polymerization was allowed to proceed as described in the previous section. To test for catalyst response to hydrogen, the EH experiments were also carried out using 300 ppm $H_2$/ethylene mixed gas.

For EP, the reactor was prepared as described above and purged with propylene. Isohexane, the scavenger solution and a predetermined amount of propylene gas were added sequentially to the reaction vessels at room temperature. The reactor was then heated to the set temperature and pressurized with the required amount of ethylene while stirring at 800 rpm, followed by injection of the catalyst slurry. The polymerization was allowed to proceed as described previously.

Propylene homopolymerizations were set up similar to EP copolymerizations less the addition of ethylene.

For propylene homopolymerization in the presence of hydrogen ($PP/H_2$), the reactor was prepared as described above and purged with 25% v/v $H_2/N_2$ gas. With an atmosphere of $H_2/N_2$ gas in the reaction vessel, isohexane, the scavenger solution and a predetermined amount of propylene gas were injected sequentially at room temperature. The reactor was then heated to the set temperature followed by injection of the catalyst slurry. The polymerization was allowed to proceed as described previously.

Polymer Characterization. Polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 μm, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 uL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC) measurements were performed on a TA-Q100 instrument to determine the melting point (Tm) of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period.

The weight percent of ethylene incorporated in polymers was determined by rapid FT-IR spectroscopy on a Bruker Equinox 55+IR in reflection mode. Samples were prepared in a thin film format by evaporative deposition techniques. FT-IR methods were calibrated using a set of samples with a range of known wt % ethylene content. For ethylene-1-octene copolymers, the wt % octene in the copolymer was determined via measurement of the methyl deformation band at ~1375 $cm^{-1}$. The peak height of this band was normalized by the combination and overtone band at ~4321 $cm^{-1}$, which corrects for path length differences.

For ethylene-propylene copolymers, the wt % ethylene is determined via measurement of the methylene rocking band (~770 $cm^{-1}$ to 700 $cm^{-1}$). The peak area of this band is normalized by sum of the band areas of the combination and overtone bands in the 4500 $cm^{-1}$ to 4000 $cm^{-1}$ range. For samples with composition outside the calibration range, the wt % ethylene was determined by $^1$H NMR spectroscopy or estimated from the polymer Tm.

$^1$H NMR data were collected at 120° C. in a 5 mm probe using a spectrometer with a $^1$H frequency of 500 MHz. Data was recorded using a maximum pulse width of 45°, 5 seconds between pulses and signal averaging 120 transients. Spectral signals were integrated. Samples were dissolved in deuterated 1,1,2,2,-tetrachloroethane at concentrations of 1-2 wt % prior to being inserted into the spectrometer magnet. Prior to data analysis, spectra were referenced by setting the residual hydrogen-containing solvent resonance to 5.98 ppm. Vinylenes were measured as the number of vinylenes per 1000 carbon atoms using the resonances between 5.5-5.31 ppm. Trisubstituted end-groups ("trisubs") were measured as the number of trisubstituted groups per 1000 carbon atoms using the resonances between 5.3-4.85 ppm, by difference from vinyls. Vinyl end-groups were measured as the number of vinyls per 1000 carbon atoms using the resonances between 5.9-5.65 and between 5.3-4.85 ppm. Vinylidene end-groups were measured as the number of vinylidenes per 1000 carbon atoms using the resonances between 4.85-4.65 ppm.

TABLE 1

Reaction conditions for ethylene homopolymerization (HDPE) and ethylene-octene copolymerization (EO) using Activator-1 or MAO.

| | |
|---|---|
| Catalyst loading | 0.020–0.080 μmol |
| Activator-1 | 1.1 equiv |
| MAO | 500 equiv |
| Temperature | 100° C. |
| Pressure Setpoint | 135 psi |
| 1-Octene | 100 μL |
| Total Volume | 5 mL |
| Solvent | Isohexane |
| Aluminum compound (scavenger) | 0.5 or 1 μmol tri-n-octyl aluminum (TNOAL) |
| Quench Value | 20 psi |
| Maximum Reaction Time | 30 in |

TABLE 2

Catalyst activity and polymer properties for ethylene homopolymerization (HDPE) and ethylene-octene copolymerization (EO) using Activator-1 or MAO.

| Entry | Run | Catalyst, umol | Activator | TNOAL umol | Polymer | time (s) | yield (g) | activity (g/mmol-hr) | Mw (kg/mol) | Mn (kg/mol) | Mw/Mn | wt % octene | Tm (° C.) |
|---|---|---|---|---|---|---|---|---|---|---|---|---|---|
| 1 | 1 | 1-Zr 0.02 | MAO | — | EO | 29.1 | 0.079 | 488,660 | 265 | 162 | 1.64 | 6.7 | 116.2 |
| 2 | 2 | 1-Zr 0.02 | MAO | — | EO | 26.5 | 0.075 | 509,434 | 268 | 155 | 1.73 | 6.2 | 117.4 |
| 3 | 1 | 1-Hf 0.02 | MAO | — | EO | 125.5 | 0.068 | 97,530 | 789 | 471 | 1.68 | 7.4 | 113.6 |
| 4 | 2 | 1-Hf 0.02 | MAO | — | EO | 113.8 | 0.064 | 101,230 | 1,101 | 642 | 1.72 | 6.3 | 113.7 |
| 5 | 1 | 2-Zr 0.02 | MAO | — | EO | 24.7 | 0.078 | 568,421 | 65 | 41 | 1.60 | 3.5 | 129.4 |
| 6 | 2 | 2-Zr 0.02 | MAO | — | EO | 24.0 | 0.068 | 510,000 | 63 | 39 | 1.60 | 3.4 | 128.5 |
| 7 | 1 | 2-Hf 0.02 | MAO | — | EO | 227.8 | 0.039 | 30,817 | 259 | 142 | 1.83 | 4.8 | 127.5 |
| 8 | 2 | 2-Hf 0.02 | MAO | — | EO | 247.1 | 0.034 | 24,767 | 307 | 195 | 1.57 | 2.7 | 128.1 |
| 9 | 1 | 3-Zr 0.02 | MAO | — | EO | 1800.7 | 0.008 | 800 | — | — | — | — | — |
| 10 | 2 | 3-Zr 0.08 | MAO | — | EO | 1800.9 | 0.030 | 750 | 211 | 100 | 2.11 | 9.1 | 112.5 |
| 11 | 1 | 3-Hf 0.02 | MAO | — | EO | 1801.1 | 0.005 | 500 | — | — | — | — | — |
| 12 | 2 | 3-Hf 0.08 | MAO | — | EO | 1800.4 | 0.004 | 100 | — | — | — | — | — |
| 13 | 1 | 1-Zr 0.02 | Activator-1 | 1 | EO | 30.1 | 0.058 | 346,844 | 241 | 148 | 1.62 | 4.1 | 119.7 |
| 14 | 2 | 1-Zr 0.02 | Activator-1 | 1 | EO | 30.9 | 0.068 | 396,117 | 235 | 130 | 1.81 | 5.0 | 119.7 |
| 15 | 1 | 1-Hf 0.02 | Activator-1 | 1 | EO | 388.3 | 0.033 | 15,297 | 855 | 479 | 1.79 | 4.9 | 117.4 |
| 16 | 2 | 1-Hf 0.02 | Activator-1 | 1 | EO | 236.8 | 0.041 | 31,166 | 890 | 572 | 1.55 | 3.9 | 120.5 |
| 17 | 1 | 2-Zr 0.02 | Activator-1 | 0.5 | EO | 34.1 | 0.060 | 316,716 | 85 | 53 | 1.61 | 3.2 | 129.4 |
| 18 | 2 | 2-Zr 0.02 | Activator-1 | 0.5 | EO | 31.7 | 0.060 | 340,694 | 82 | 47 | 1.74 | 3.4 | 129.7 |
| 19 | 1 | 2-Hf 0.02 | Activator-1 | 0.5 | EO | 591.8 | 0.030 | 9,125 | 442 | 270 | 1.64 | 2.6 | 127.9 |
| 20 | 2 | 2-Hf 0.02 | Activator-1 | 0.5 | EO | 688.7 | 0.030 | 7,841 | 452 | 292 | 1.55 | 3.0 | 129.3 |
| 21 | 1 | 3-Zr 0.02 | Activator-1 | 0.5 | EO | 1800.7 | 0.001 | 100 | — | — | — | — | — |
| 22 | 2 | 3-Zr 0.08 | Activator-1 | 0.5 | EO | 1800.9 | 0.006 | 150 | — | — | — | — | — |
| 23 | 1 | 3-Hf 0.02 | Activator-1 | 0.5 | EO | 1800.2 | 0.000 | 0 | — | — | — | — | — |
| 24 | 2 | 3-Hf 0.08 | Activator-1 | 0.5 | EO | 1086.2 | 0.044 | 1,823 | 328 | 204 | 1.61 | 5.7 | 114.9 |
| 25 | 1 | 1-Zr 0.02 | Activator-1 | 1 | HDPE | 31.4 | 0.056 | 321,019 | 243 | 151 | 1.61 | NA | 135.7 |
| 26 | 2 | 1-Zr 0.02 | Activator-1 | 1 | HDPE | 53.6 | 0.054 | 181,343 | 253 | 155 | 1.64 | NA | 135.8 |
| 27 | 1 | 1-Hf 0.02 | Activator-1 | 1 | HDPE | 459.9 | 0.037 | 14,481 | 965 | 575 | 1.68 | NA | 135.7 |
| 28 | 1 | 2-Zr 0.02 | Activator-1 | 0.5 | HDPE | 1801.0 | 0.000 | 0 | — | — | — | NA | — |
| 29 | 2 | 2-Zr 0.08 | Activator-1 | 0.5 | HDPE | 1801.0 | 0.003 | 75 | — | — | — | NA | — |
| 30 | 1 | 2-Hf 0.02 | Activator-1 | 0.5 | HDPE | 1800.2 | 0.000 | 0 | — | — | — | NA | — |
| 31 | 2 | 2-Hf 0.08 | Activator-1 | 0.5 | HDPE | 1801.1 | 0.010 | 250 | — | — | — | NA | — |
| 32 | 1 | 3-Zr 0.02 | Activator-1 | 0.5 | HDPE | 35.3 | 0.065 | 331,445 | 91 | 55 | 1.66 | NA | 135.5 |
| 33 | 2 | 3-Zr 0.02 | Activator-1 | 0.5 | HDPE | 31.3 | 0.058 | 333,546 | 92 | 58 | 1.59 | NA | 135.5 |
| 34 | 1 | 3-Hf 0.02 | Activator-1 | 0.5 | HDPE | 483.3 | 0.035 | 13,035 | 535 | 335 | 1.60 | NA | 137.8 |
| 35 | 2 | 3-Hf 0.02 | Activator-1 | 0.5 | HDPE | 571.7 | 0.032 | 10,075 | 510 | 285 | 1.79 | NA | 137.4 |

TABLE 3

Reaction conditions for propylene homopolymerization (PP) using Activator-1 or MAO.

| | |
|---|---|
| Catalyst loading | 0.040 μmol |
| Activator-1 | 1.1 equiv |
| MAO | 500 equiv |
| Temperature | 70° C. |
| Propylene Pressure | 120 psi |
| Total Volume | 4 mL |
| Solvent | Isohexane |
| Aluminum compound (scavenger) | 0.3 μmol tri-n-octyl aluminum (TNOAL) |
| Quench Value | 3 psi |
| Maximum Reaction Time | 20 in |

TABLE 4

Catalyst activity and polymer properties for propylene homopolymerization (PP) using Activator-1 or MAO.

| Entry | Run | Catalyst | Activator | TNOAL umol | time (s) | yield (g) | activity (g/mmol-hr) | Mw (kg/mol) | Mn (kg/mol) | Mw/Mn | Tm (° C.) |
|---|---|---|---|---|---|---|---|---|---|---|---|
| 1 | 1 | 1-Zr | Activator-1 | 0.3 | 101.9 | 0.053 | 46,811 | 259 | 153 | 1.69 | 160.0 |
| 2 | 2 | 1-Zr | Activator-1 | 0.3 | 97.3 | 0.050 | 46,249 | 253 | 156 | 1.62 | 158.8 |
| 3 | 1 | 1-Hf | Activator-1 | 0.3 | 1072.7 | 0.010 | 839 | 97 | 61 | 1.59 | 161.4 |
| 4 | 2 | 1-Hf | Activator-1 | 0.3 | 1020.6 | 0.011 | 970 | 103 | 65 | 1.58 | 160.5 |
| 5 | 1 | 2-Zr | Activator-1 | 0.3 | 1200.4 | 0.000 | 0 | — | — | — | — |
| 6 | 2 | 2-Zr | Activator-1 | 0.3 | 1200.6 | 0.000 | 0 | — | — | — | — |
| 7 | 1 | 2-Hf | Activator-1 | 0.3 | 1200.3 | 0.004 | 300 | — | — | — | — |
| 8 | 2 | 2-Hf | Activator-1 | 0.3 | 1201.0 | 0.004 | 300 | — | — | — | — |
| 9 | 1 | 1-Zr | MAO | — | 49.2 | 0.096 | 175,610 | 367 | 222 | 1.65 | 157.4 |
| 10 | 2 | 1-Zr | MAO | — | 50.4 | 0.096 | 171,429 | 371 | 232 | 1.60 | 157.9 |
| 11 | 1 | 1-Hf | MAO | — | 595.9 | 0.036 | 5,437 | 120 | 68 | 1.76 | 154.1 |
| 12 | 2 | 1-Hf | MAO | — | 506.4 | 0.037 | 6,576 | 161 | 91 | 1.77 | 155.1 |
| 13 | 1 | 2-Zr | MAO | — | 1200.7 | 0.002 | 150 | — | — | — | — |
| 14 | 2 | 2-Zr | MAO | — | 1200.2 | 0.003 | 225 | — | — | — | — |
| 15 | 1 | 2-Hf | MAO | — | 1200.3 | 0.009 | 675 | — | — | — | — |
| 16 | 2 | 2-Hf | MAO | — | 1201.2 | 0.010 | 749 | 19 | 12 | 1.60 | 101.7 |

TABLE 5

Reaction conditions for ethylene-propylene copolymerization (EP) using Activator-1.

| | |
|---|---|
| Catalyst loading | 0.015 μmol |
| Activator-1 | 1.1 equiv |
| Temperature | 110° C. |
| Ethylene Pressure | 125 psi |
| Propylene Pressure | 125 or 185 psi |
| Total Volume | 5.1 mL |
| Solvent | Isohexane |
| Aluminum compound (scavenger) | 0.5 μmol tri-n-octyl aluminum (TNOAL) |
| Quench Value | 4 psi |
| Maximum Reaction Time | 30 in |

TABLE 6

Catalyst activity and polymer properties for ethylene-propylene copolymerization (EP) using Activator-1.

| Entry | Run | Catalyst | TNOAL umol | C3 Pressure (psi) | C2 Pressure (psi) | time (s) | yield (g) | activity (g/mmol-hr) | Mw (kg/mol) | Mn (kg/mol) | Mw/Mn | wt % propylene (est from Tm) | Tm (° C.) |
|---|---|---|---|---|---|---|---|---|---|---|---|---|---|
| 1 | 1 | 1-Zr | 0.5 | 125 | 125 | 15.4 | 0.043 | 670,565 | 242 | 154 | 1.57 | 11 | 105.9 |
| 2 | 2 | 1-Zr | 0.5 | 125 | 125 | 18.0 | 0.037 | 493,608 | 283 | 167 | 1.70 | 11 | 105.4 |
| 3 | 3 | 1-Zr | 0.5 | 125 | 125 | 14.2 | 0.042 | 709,859 | 243 | 146 | 1.67 | 11 | 107.2 |
| 4 | 1 | 1-Zr | 0.5 | 185 | 125 | 25.4 | 0.041 | 386,792 | 272 | 160 | 1.70 | 14 | 94.7 |
| 5 | 2 | 1-Zr | 0.5 | 185 | 125 | 37.7 | 0.025 | 159,025 | 271 | 161 | 1.68 | 15 | 93.6 |
| 6 | 3 | 1-Zr | 0.5 | 185 | 125 | 26.7 | 0.039 | 351,088 | 262 | 167 | 1.57 | 14 | 95.1 |
| 7 | 1 | 1-Hf | 0.5 | 125 | 125 | 112.4 | 0.016 | 34,158 | 585 | 353 | 1.66 | 12 | 101.7 |
| 8 | 2 | 1-Hf | 0.5 | 125 | 125 | 102.8 | 0.017 | 39,704 | 891 | 479 | 1.86 | 12 | 101.6 |
| 9 | 3 | 1-Hf | 0.5 | 125 | 125 | 280.6 | 0.013 | 11,120 | 710 | 447 | 1.59 | 16 | 88.1 |
| 10 | 1 | 1-Hf | 0.5 | 185 | 125 | 184.6 | 0.017 | 22,102 | 583 | 322 | 1.81 | 16 | 90.0 |
| 11 | 2 | 1-Hf | 0.5 | 185 | 125 | 148.9 | 0.018 | 29,015 | 498 | 282 | 1.77 | 15 | 91.4 |

TABLE 7

Reaction conditions for ethylene-hexene copolymerization (EH) using supported catalysts.

| | |
|---|---|
| Catalyst loading | 0.012 μmol of metal complex |
| Temperature | 85° C. |
| Pressure Setpoint | 130 psi |
| 1-hexene | 30, 180 or 300 μL |
| Total Volume | 5 mL |
| Solvent | Isohexane |
| Aluminum compound (scavenger) | 4 μmol tri-n-octyl aluminum (TNOAL) |
| Quench Value | 55 psi |
| Maximum Reaction Time | 45 min |

TABLE 8

Catalyst activity and polymer properties for ethylene-hexene copolymerization (EH) using supported catalysts.

| Entry | Run | Catalyst | hexene uL | time (s) | yield (g) | activity (g/mmol-hr) | Mw (kg/mol) | Mn (kg/mol) | Mw/Mn | wt % C6 | Tm (° C.) |
|---|---|---|---|---|---|---|---|---|---|---|---|
| 1 | 1 | 1-Zr_s | 30 | 2701 | 0.020 | 2222 | 451 | 121 | 3.7 | 1.6 | 130 |
| 2 | 2 | 1-Zr_s | 30 | 2700 | 0.025 | 2777 | 538 | 110 | 4.9 | 0.7 | 130 |
| 3 | 1 | 1-Hf_s | 30 | 2300 | 0.072 | 9392 | 2372 | 1220 | 1.9 | 1.8 | 127 |
| 4 | 2 | 1-Hf_s | 30 | 2701 | 0.080 | 8887 | 2303 | 960 | 2.4 | 1.2 | 126 |
| 5 | 1 | 1-Zr_s | 180 | 2352 | 0.059 | 7526 | 224 | 101 | 2.2 | 6.2 | 120 |
| 6 | 2 | 1-Zr_s | 180 | 2700 | 0.070 | 7777 | 465 | 126 | 3.7 | 6.4 | 119 |
| 7 | 1 | 1-Hf_s | 180 | 1086 | 0.097 | 26801 | 2176 | 1196 | 1.8 | 8.3 | 112 |
| 8 | 2 | 1-Hf_s | 180 | 1212 | 0.092 | 22782 | 2111 | 1116 | 1.9 | 7.7 | 113 |
| 9 | 1 | 1-Zr_s | 300 | 844 | 0.085 | 30228 | 237 | 120 | 2.0 | 8.3 | 112 |
| 10 | 2 | 1-Zr_s | 300 | 1798 | 0.092 | 15347 | 250 | 110 | 2.3 | 9.0 | 112 |
| 11 | 1 | 1-Hf_s | 300 | 791 | 0.097 | 36770 | 1788 | 995 | 1.8 | 11.5 | 101 |
| 12 | 2 | 1-Hf_s | 300 | 830 | 0.094 | 33980 | 1836 | 1045 | 1.8 | 11.8 | 101 |

TABLE 9

Reaction conditions for propylene homopolymerization (PP) using supported catalysts.

| | |
|---|---|
| Catalyst loading | 0.015 µmol of metal complex |
| Temperature | 70° C. |
| Propylene Pressure | 115 psi |
| Total Volume | 5 mL |
| Solvent | Isohexane |
| Aluminum compound (scavenger) | 4 µmol tri-n-octyl aluminum (TNOAL) |
| Quench Value | 15 psi |
| Maximum Reaction Time | 45 in |

TABLE 10

Catalyst activity and polymer properties for propylene homopolymerization (PP) using supported catalysts.

| Entry | Run | Catalyst | Experiment | time (s) | yield (g) | activity (g/mmol-hr) | Mw (kg/mol) | Mn (kg/mol) | Mw/Mn | Tm (° C.) |
|---|---|---|---|---|---|---|---|---|---|---|
| 1 | 1 | 1-Zr_s | PP | 2700.4 | 0.008 | 711 | — | — | — | — |
| 2 | 2 | 1-Zr_s | PP | 2700.5 | 0.011 | 978 | 72 | 39 | 1.845 | 158.8 |
| 3 | 1 | 1-Hf_s | PP | 2700.7 | 0.012 | 1,066 | 142 | 80 | 1.773 | 161.5 |
| 4 | 2 | 1-Hf_s | PP | 2700.6 | 0.014 | 1,244 | 149 | 76 | 1.959 | 162.8 |
| 5 | 1 | 1-Zr_s | PP/H2 | 2700.8 | 0.012 | 1,066 | 34 | 15 | 2.281 | 155.4 |
| 6 | 2 | 1-Zr_s | PP/H2 | 2700.2 | 0.015 | 1,333 | 37 | 19 | 1.951 | 156.0 |
| 7 | 1 | 1-Hf_s | PP/H2 | 2700.8 | 0.012 | 1,066 | 85 | 46 | 1.83 | 160.6 |
| 8 | 2 | 1-Hf_s | PP/H2 | 2700.2 | 0.014 | 1,244 | 78 | 43 | 1.835 | 161.4 |

TABLE 11

Reaction conditions for ethylene-propylene copolymerization (EP) using supported catalysts.

| | |
|---|---|
| Catalyst loading | 0.015 µmol of metal complex |
| Temperature | 70° C. |
| Propylene Pressure | 115 psi |
| Ethylene Pressure | 125 psi |
| Total Volume | 5 mL |
| Solvent | Isohexane |
| Aluminum compound (scavenger) | 4 µmol tri-n-octyl aluminum (TNOAL) |
| Quench Value | 15 psi |
| Maximum Reaction Time | 45 in |

TABLE 12

Catalyst activity and polymer properties for ethylene-propylene copolymerization (EP) using supported catalysts.

| Entry | Run | Catalyst | time (s) | yield (g) | activity (g/mmol-hr) | Mw (kg/mol) | Mn (kg/mol) | Mw/Mn | wt % propylene ($^1$H NMR) | Tm (° C.) |
|---|---|---|---|---|---|---|---|---|---|---|
| 1 | 1 | 1-Zr_s | 190.2 | 0.072 | 90,852 | 194 | 122 | 1.588 | — | 45.4 |
| 2 | 2 | 1-Zr_s | 149.9 | 0.083 | 132,889 | 248 | 150 | 1.652 | 25.8 | — |
| 3 | 1 | 1-Hf_s | 356.7 | 0.058 | 39,024 | 1,344 | 801 | 1.678 | — | 59.1 |
| 4 | 2 | 1-Hf_s | 294.7 | 0.065 | 52,935 | 2,299 | 1,525 | 1.508 | 23.0 | 61.3 |

TABLE 13

Reaction conditions for ethylene-octene copolymerization (EO) using various chain transfer agents (CTA).

| | |
|---|---|
| Catalyst loading | 0.020 μmol |
| Temperature | 100° C. |
| Pressure Setpoint | 135 psi |
| 1-Octene | 100 μL |
| Total Volume | 5 mL |
| Solvent | Isohexane |
| Chain Transfer Agent | variable |
| Quench Value | 20 psi |
| Maximum Reaction Time | 30 in |

TABLE 14

Catalyst activity and polymer properties for ethylene-octene copolymerization (EO) using various CTAs.

| Entry | Run | Catalyst | CTA | nmol Al or Zn | time (s) | yield (g) | activity (g/mmol-hr) | Mw corr (kg/mol) | Mn corr (kg/mol) | Mw/Mn | wt % octene | Tm (° C.) |
|---|---|---|---|---|---|---|---|---|---|---|---|---|
| 1 | 1 | 1-Zr | diethylzinc | 400 | 30 | 0.088 | 526246 | 97 | 56 | 1.7 | 6.6 | 118 |
| 2 | 2 | 1-Zr | diethylzinc | 400 | 25 | 0.085 | 621951 | 100 | 60 | 1.7 | 4.6 | 119 |
| 3 | 1 | 1-Zr | diethylzinc | 1600 | 23 | 0.076 | 602643 | 51 | 30 | 1.7 | 4.5 | 122 |
| 4 | 2 | 1-Zr | diethylzinc | 1600 | 24 | 0.071 | 532500 | 51 | 32 | 1.6 | 2.8 | 124 |
| 5 | 1 | 1-Zr | diethylzinc | 2800 | 25 | 0.067 | 474803 | 37 | 22 | 1.7 | 4.3 | 126 |
| 6 | 2 | 1-Zr | diethylzinc | 2800 | 26 | 0.070 | 492188 | 35 | 21 | 1.7 | 3.3 | 127 |
| 7 | 1 | 1-Zr | diethylzinc | 4000 | 23 | 0.069 | 533047 | 28 | 15 | 2.0 | 3.6 | 129 |
| 8 | 2 | 1-Zr | diethylzinc | 4000 | 22 | 0.065 | 531818 | 29 | 16 | 1.8 | 2.7 | 132 |
| 9 | 1 | 1-Zr | TNOAL | 400 | 31 | 0.092 | 539414 | 142 | 86 | 1.7 | 3.7 | 118 |
| 10 | 2 | 1-Zr | TNOAL | 400 | 29 | 0.092 | 567123 | 137 | 75 | 1.8 | 4.7 | 118 |
| 11 | 1 | 1-Zr | TNOAL | 1600 | 23 | 0.082 | 650220 | 112 | 61 | 1.8 | 6.8 | 119 |
| 12 | 2 | 1-Zr | TNOAL | 1600 | 23 | 0.075 | 576923 | 113 | 66 | 1.7 | 4.7 | 119 |
| 13 | 1 | 1-Zr | TNOAL | 2800 | 23 | 0.078 | 618502 | 100 | 50 | 2.0 | 4.5 | 120 |
| 14 | 2 | 1-Zr | TNOAL | 2800 | 21 | 0.079 | 667606 | 94 | 45 | 2.1 | 4.2 | 120 |
| 15 | 1 | 1-Zr | TNOAL | 4000 | 24 | 0.073 | 549791 | 86 | 45 | 1.9 | 3.9 | 122 |
| 16 | 2 | 1-Zr | TNOAL | 4000 | 21 | 0.075 | 630841 | 83 | 47 | 1.8 | 3.6 | 124 |
| 17 | 1 | 1-Zr | DIBALO | 400 | 30 | 0.087 | 516832 | 148 | 87 | 1.7 | 5.8 | 118 |
| 18 | 2 | 1-Zr | DIBALO | 400 | 32 | 0.086 | 486792 | 146 | 84 | 1.7 | 5.2 | 118 |
| 19 | 1 | 1-Zr | DIBALO | 1600 | 25 | 0.082 | 583399 | 147 | 85 | 1.7 | 4.9 | 118 |
| 20 | 2 | 1-Zr | DIBALO | 1600 | 26 | 0.083 | 568061 | 137 | 73 | 1.9 | 4.4 | 119 |
| 21 | 1 | 1-Zr | DIBALO | 2800 | 26 | 0.081 | 556489 | 138 | 79 | 1.8 | 5.3 | 119 |
| 22 | 2 | 1-Zr | DIBALO | 2800 | 26 | 0.083 | 574615 | 137 | 71 | 1.9 | 4.5 | 120 |
| 23 | 1 | 1-Zr | DIBALO | 4000 | 25 | 0.086 | 619200 | 141 | 79 | 1.8 | 4.7 | 122 |
| 24 | 2 | 1-Zr | DIBALO | 4000 | 24 | 0.084 | 643404 | 131 | 72 | 1.8 | 3.4 | 124 |
| 25 | 1 | 1-Hf | diethylzinc | 400 | 179 | 0.048 | 48376 | 110 | 69 | 1.6 | 4.0 | 121 |
| 26 | 2 | 1-Hf | diethylzinc | 400 | 164 | 0.046 | 50396 | 100 | 60 | 1.7 | 3.5 | 121 |
| 27 | 1 | 1-Hf | diethylzinc | 1600 | 224 | 0.044 | 35373 | 44 | 28 | 1.6 | 3.4 | 124 |
| 28 | 2 | 1-Hf | diethylzinc | 1600 | 369 | 0.040 | 19528 | 36 | 20 | 1.8 | 5.1 | 124 |
| 29 | 1 | 1-Hf | diethylzinc | 2800 | 427 | 0.037 | 15590 | 25 | 14 | 1.7 | 4.0 | 128 |
| 30 | 2 | 1-Hf | diethylzinc | 2800 | 277 | 0.041 | 26681 | 25 | 13 | 1.9 | 3.8 | 128 |
| 31 | 1 | 1-Hf | diethylzinc | 4000 | 310 | 0.034 | 19729 | 18 | 8 | 2.2 | 3.8 | 130 |
| 32 | 2 | 1-Hf | diethylzinc | 4000 | 304 | 0.038 | 22500 | 18 | 10 | 1.8 | 5.0 | 128 |
| 33 | 1 | 1-Hf | TNOAL | 400 | 378 | 0.086 | 40942 | 606 | 351 | 1.7 | 6.6 | 114 |
| 34 | 2 | 1-Hf | TNOAL | 400 | 299 | 0.077 | 46386 | 684 | 428 | 1.6 | 5.1 | 115 |
| 35 | 1 | 1-Hf | TNOAL | 1600 | 154 | 0.050 | 58480 | 427 | 247 | 1.7 | 4.9 | 117 |
| 36 | 2 | 1-Hf | TNOAL | 1600 | 157 | 0.049 | 56036 | 412 | 249 | 1.7 | 4.5 | 117 |
| 37 | 1 | 1-Hf | TNOAL | 2800 | 174 | 0.047 | 48593 | 326 | 188 | 1.7 | 4.6 | 119 |
| 38 | 2 | 1-Hf | TNOAL | 2800 | 182 | 0.045 | 44579 | 296 | 163 | 1.8 | 4.0 | 120 |
| 39 | 1 | 1-Hf | TNOAL | 4000 | 173 | 0.041 | 42733 | 289 | 149 | 1.9 | 3.7 | 122 |
| 40 | 2 | 1-Hf | TNOAL | 4000 | 201 | 0.042 | 37556 | 236 | 130 | 1.8 | 3.7 | 122 |
| 41 | 1 | 1-Hf | DIBALO | 400 | 567 | 0.092 | 29201 | 688 | 379 | 1.8 | 6.5 | 113 |
| 42 | 2 | 1-Hf | DIBALO | 400 | 189 | 0.059 | 56101 | 787 | 474 | 1.7 | 4.6 | 115 |
| 43 | 1 | 1-Hf | DIBALO | 1600 | 402 | 0.086 | 38527 | 753 | 452 | 1.7 | 4.9 | 115 |
| 44 | 2 | 1-Hf | DIBALO | 1600 | 168 | 0.053 | 56752 | 763 | 437 | 1.7 | 5.6 | 117 |
| 45 | 1 | 1-Hf | DIBALO | 2800 | 217 | 0.066 | 54822 | 744 | 377 | 2.0 | 3.5 | 119 |
| 46 | 2 | 1-Hf | DIBALO | 2800 | 147 | 0.048 | 58856 | 774 | 386 | 2.0 | 3.4 | 120 |

TABLE 14-continued

Catalyst activity and polymer properties for ethylene-octene copolymerization (EO) using various CTAs.

| Entry | Run | Catalyst | CTA | nmol Al or Zn | time (s) | yield (g) | activity (g/mmol-hr) | Mw corr (kg/mol) | Mn corr (kg/mol) | Mw/Mn | wt % octene | Tm (° C.) |
|---|---|---|---|---|---|---|---|---|---|---|---|---|
| 47 | 1 | 1-Hf | DIBALO | 4000 | 183 | 0.053 | 52131 | 789 | 391 | 2.0 | 2.7 | 122 |
| 1-48 | 2 | 1-Hf | DIBALO | 4000 | 180 | 0.057 | 57095 | 824 | 495 | 1.7 | 3.1 | 122 |

DIBALO is bis(diisobutylaluminum)oxide.
Entries 1-8 and 25-32 had 300 nmol of TNOAL in addition to the diethylzinc reagent.
Mw corr and Mn corr correspond to the GPC values (based on polystyrene standards) for Mw and Mn, respectively, divided by 2 to correct for EO.

The procedure of Tables 3 and 4 was repeated except that the temperature was 85 or 100° C. and the setpoint pressure is 130 or 140 psi, as indicated in Table 15. The data are presented in Table 15.

TABLE 15

Propylene Polymerization Using Activator-1.

| Catalyst | T (° C.) | P set point (psi) | Uptake psig | time (s) | Yield (g) | activity (kg/mmol-hr) | Mw (g/mol) | Mn (g/mol) | Mw/Mn | Tm (° C.) | Hf (J/g) |
|---|---|---|---|---|---|---|---|---|---|---|---|
| 1-Zr | 85 | 130 | 4.7 | 1097.3 | 0.045 | 4 | 95 | 59 | 1.6 | 158.7 | 158 |
|  |  |  | 4.7 | 1096.1 | 0.045 | 4 | 91 | 54 | 1.7 | 158.0 | 153 |
|  | 100 | 140 | 0.9 | 1054.7 | 0.012 | 1 | 36 | 23 | 1.6 | 153.1 | 91 |
|  |  |  | 0.6 | 957.7 | 0.012 | 1 | 35 | 20 | 1.7 | 154.1 | 154 |
| 1-Hf | 85 | 130 | 1.5 | 1018.1 | 0.008 | 1 | — | — | — | — | — |
|  |  |  | 1.1 | 949.2 | 0.008 | 1 | — | — | — | — | — |
|  | 100 | 140 | 0.8 | 907.8 | 0.004 | 0 | — | — | — | — | — |
|  |  |  | 0.9 | 973.5 | 0.004 | 0 | — | — | — | — | — |

Figure 2:
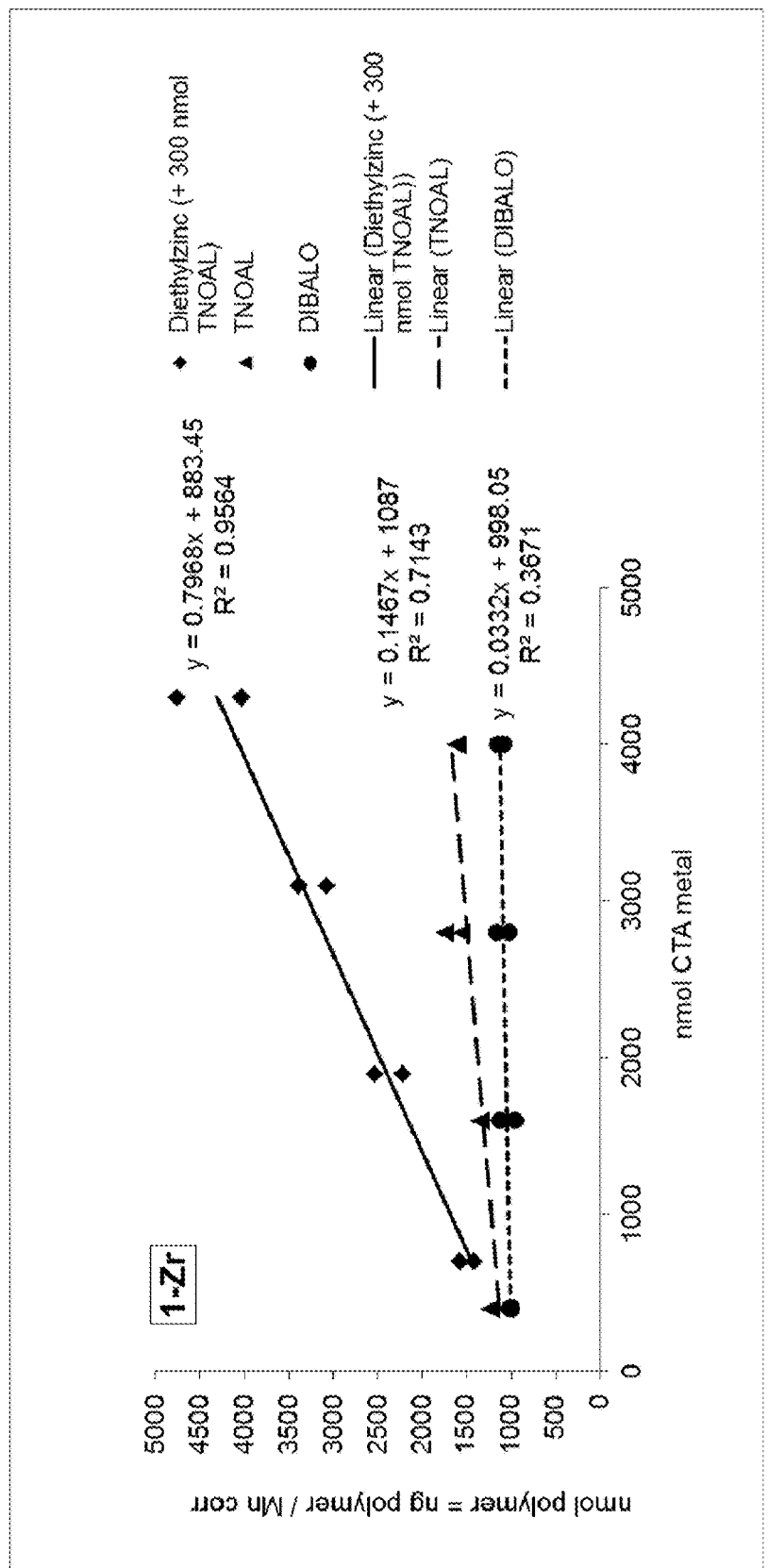
FIG. 2 is a plot of the chain transfer efficiency of catalyst 1-Zr from Table 14, which is based on the number of polymer chains transferred to each mole of metal of the chain transfer agent.

FIG. 2 shows chain transfer efficiency of 1-Zr (data from Table 14, Entries 1-24). The equation and coefficient of determination of the linear fits (least squared fit, Microsoft™ Excel 2010) are included in the figure. The slope of the linear fit corresponds to the number of chains transferred to the CTA metal (per metal). The figure shows that diethylzinc is an effective CTA with 1-Zr.

Figure 3:
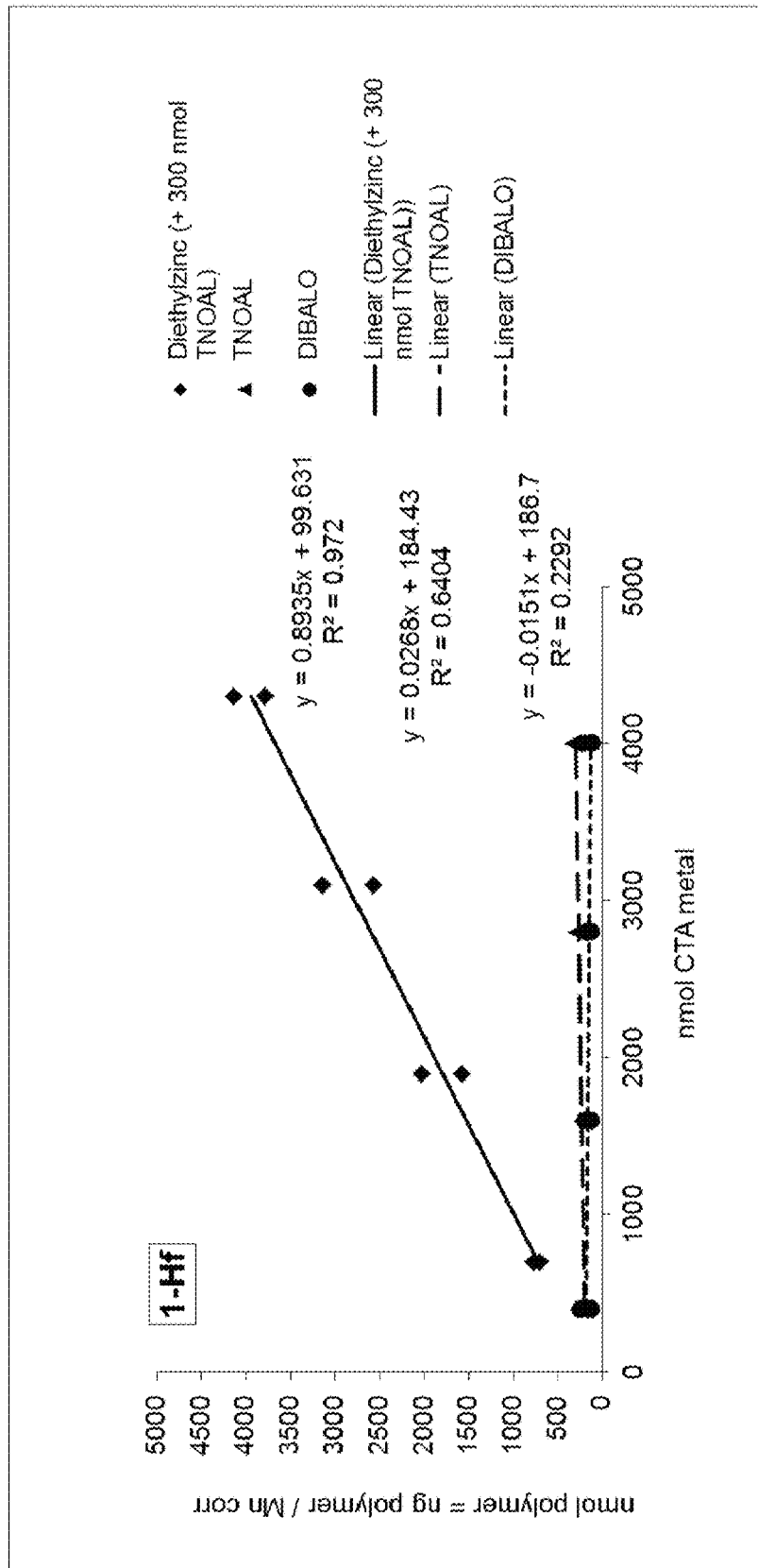
FIG. 3 is a plot of the chain transfer efficiency of catalyst 1-Hf from Table 14 which is based on the number of polymer chains transferred to each mole of metal of the chain transfer agent.
Figure 4:
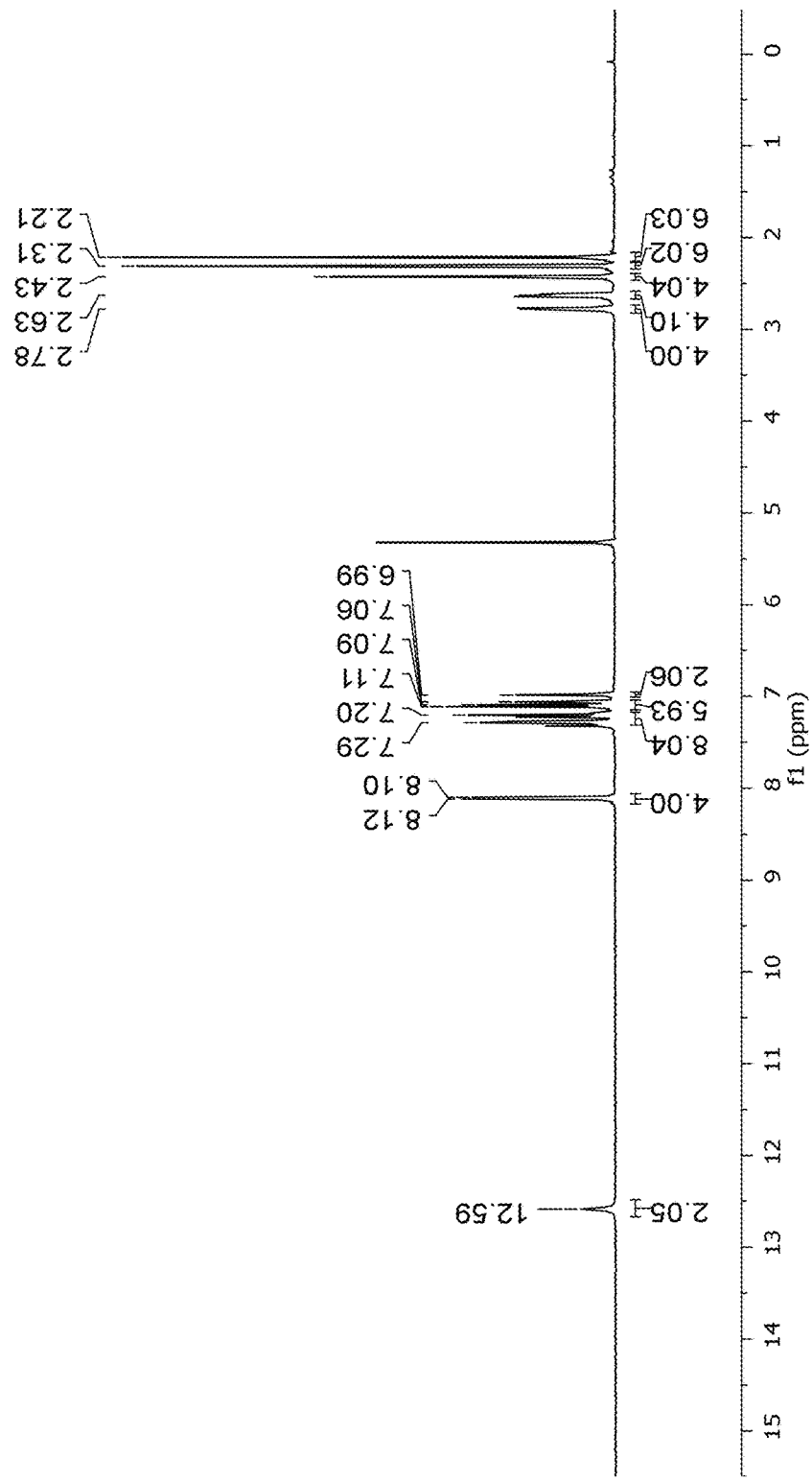
FIG. 4 is the $^1$HNMR spectrum for compound A-6 in $CD_2Cl_2$.
Figure 5:
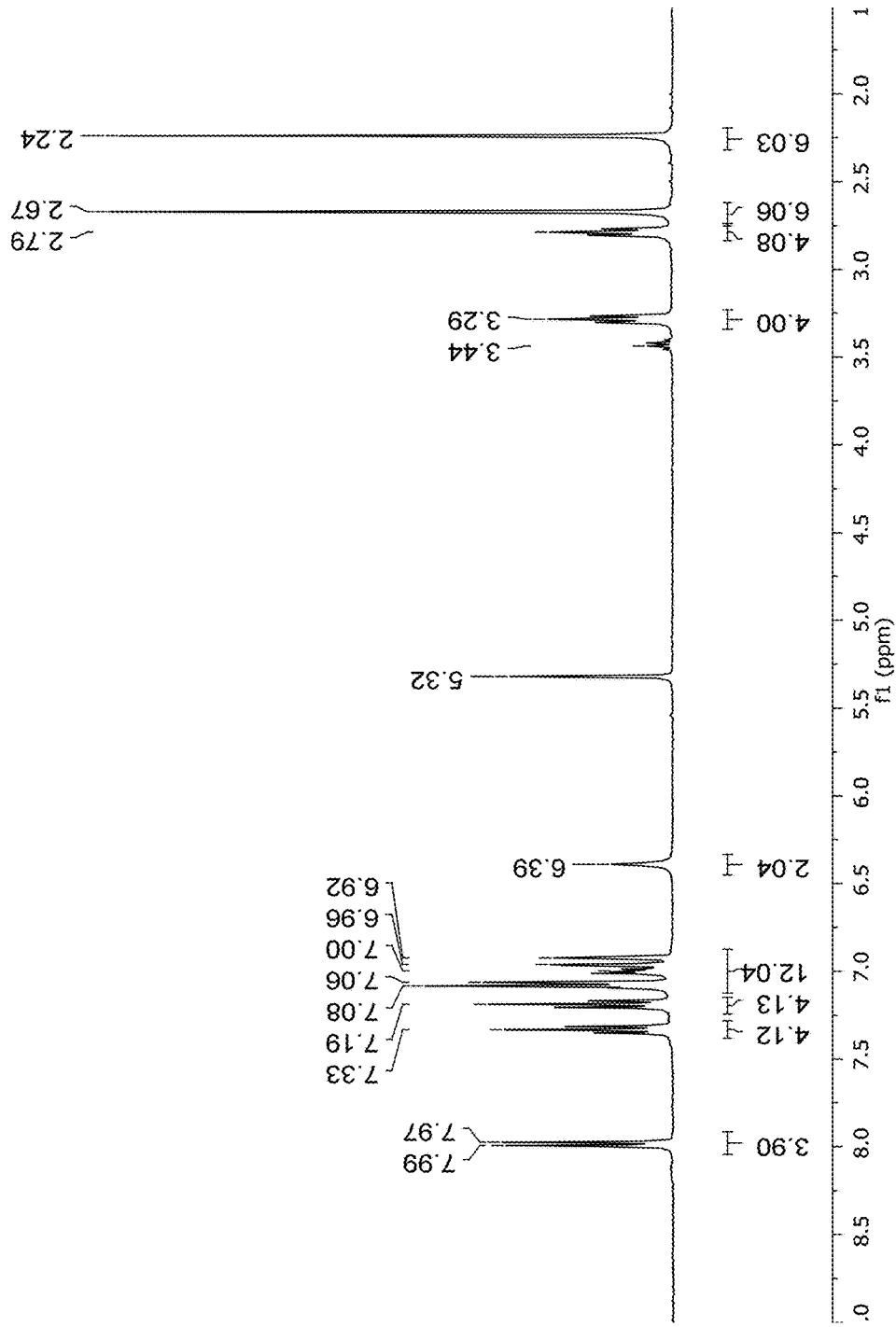
FIG. 5 is the $^1$HNMR spectrum for compound B-4 in $CD_2Cl_2$.
Figure 6:
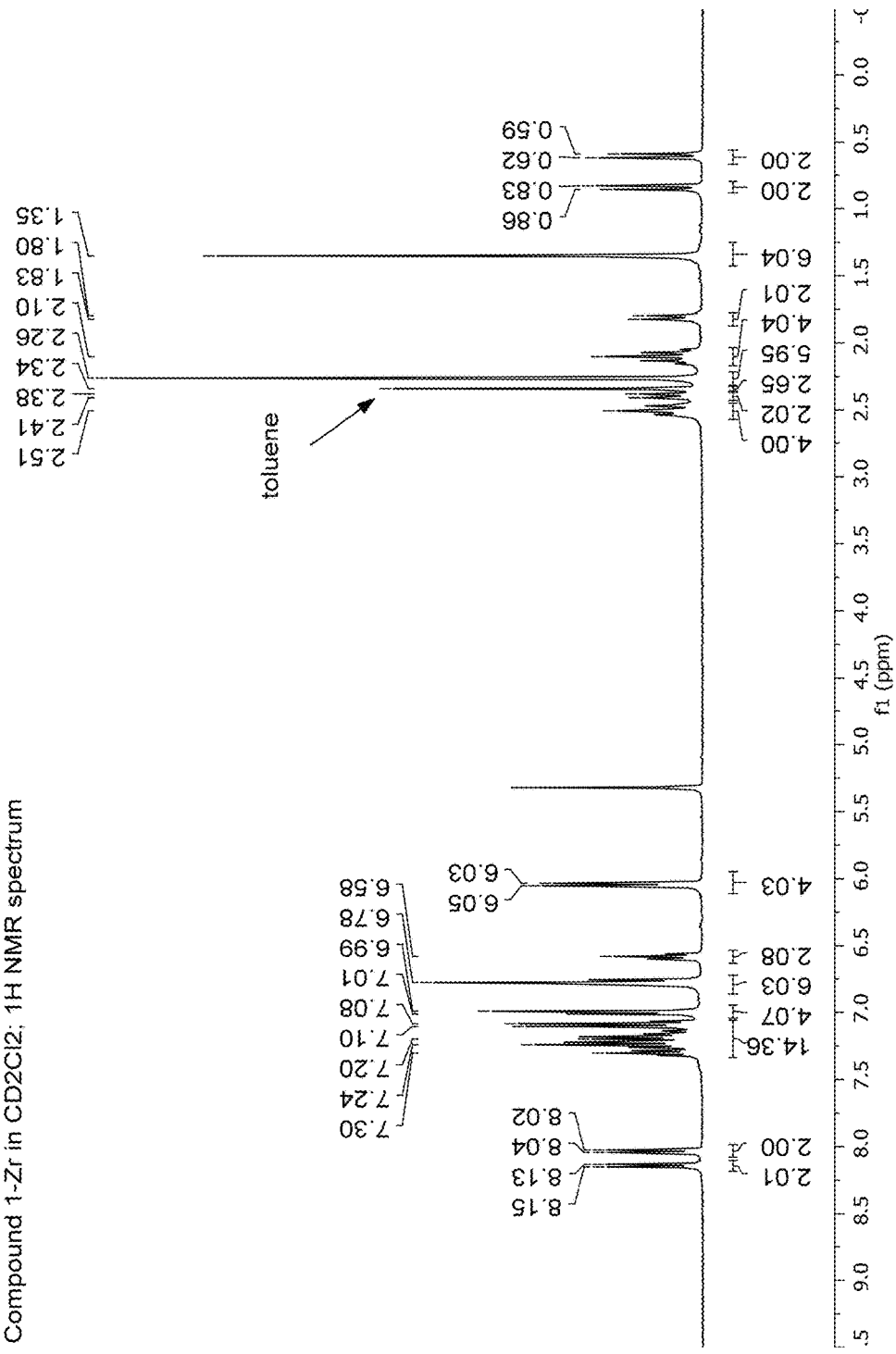
FIG. 6 is the $^1$HNMR spectrum for compound 1-Zr in $CD_2Cl_2$.
Figure 7:
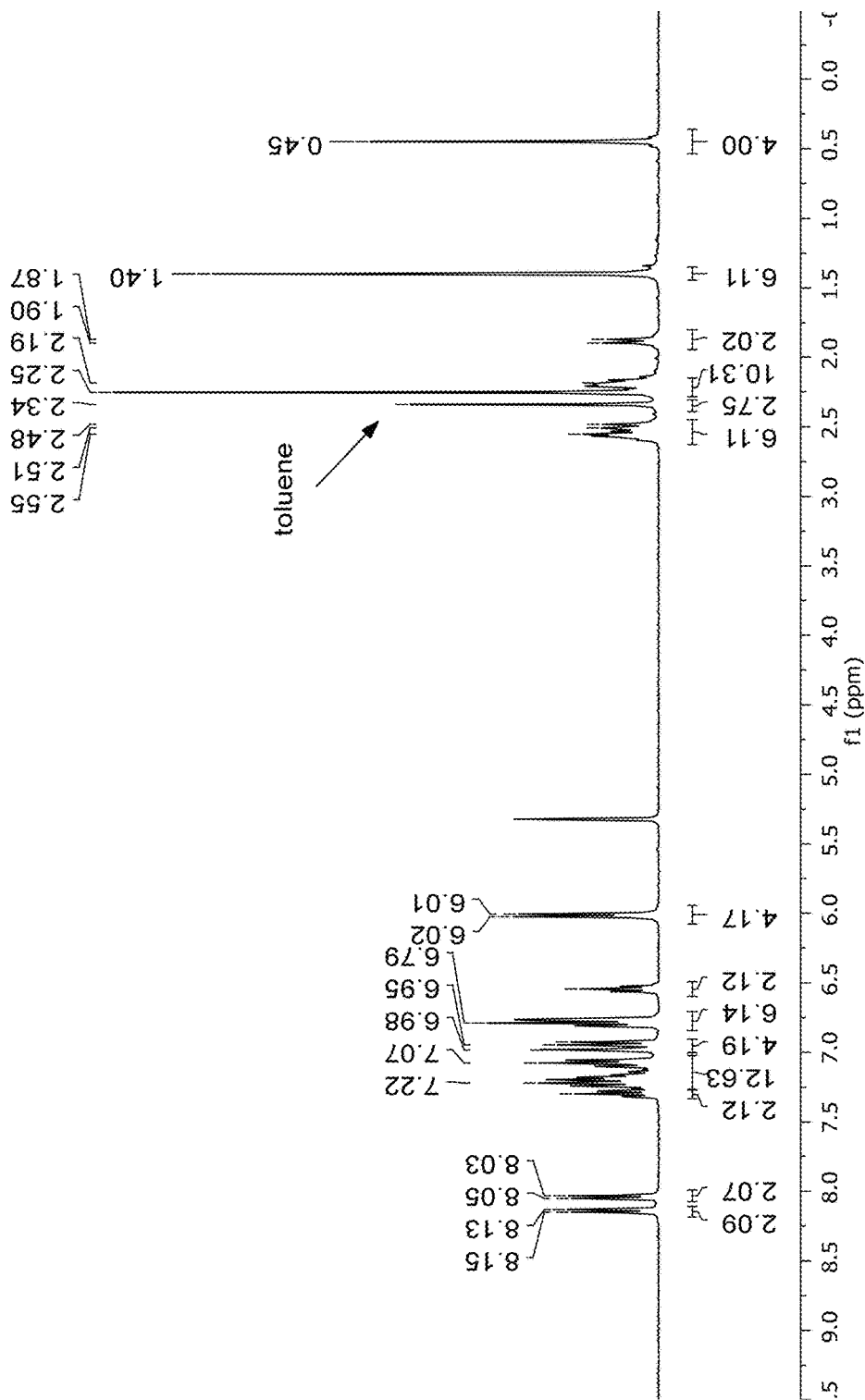
FIG. 7 is the $^1$HNMR spectrum for compound 1-Hf in $CD_2Cl_2$.
Figure 8:
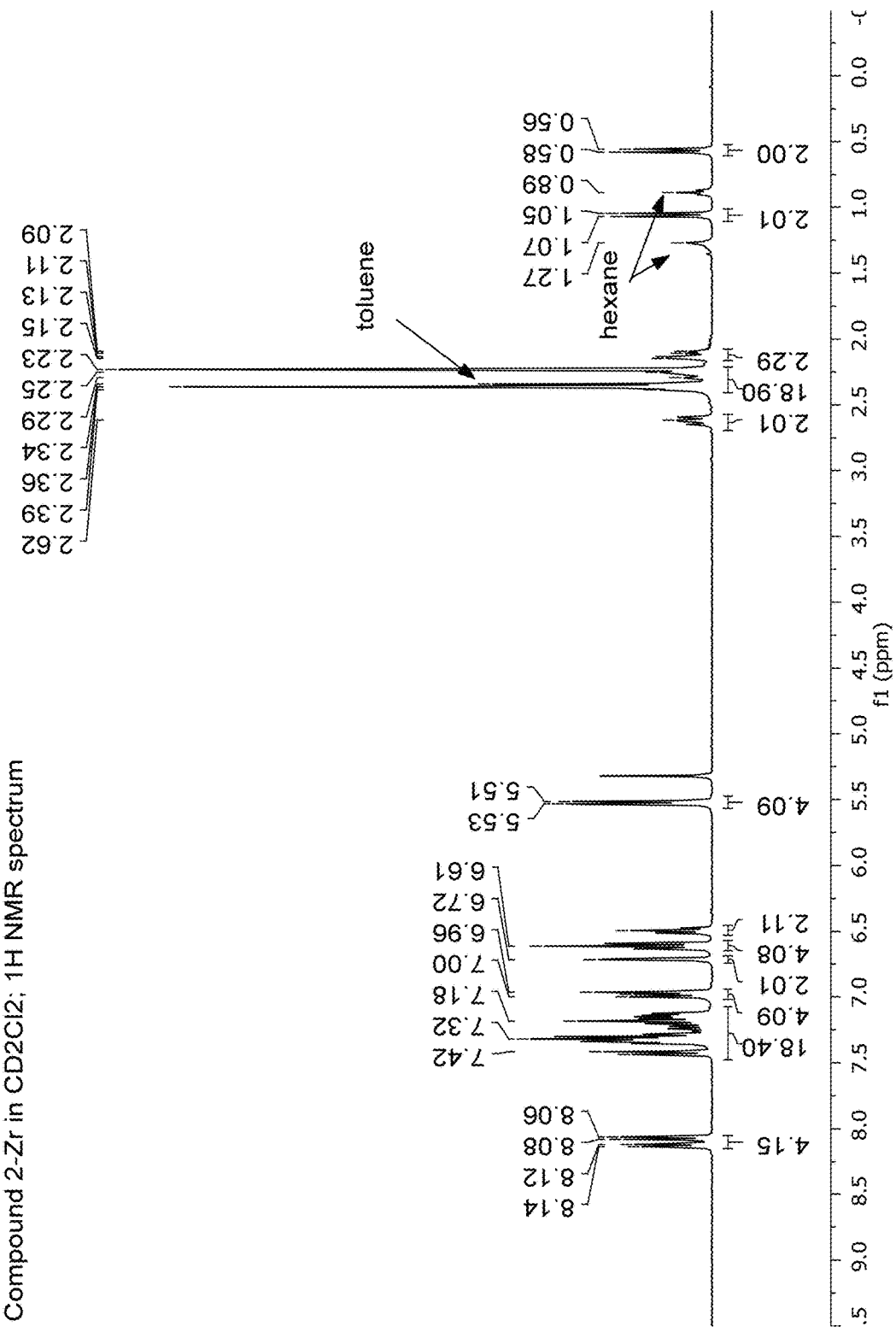
FIG. 8 is the $^1$HNMR spectrum for compound 2-Zr in $CD_2Cl_2$.
Figure 9:
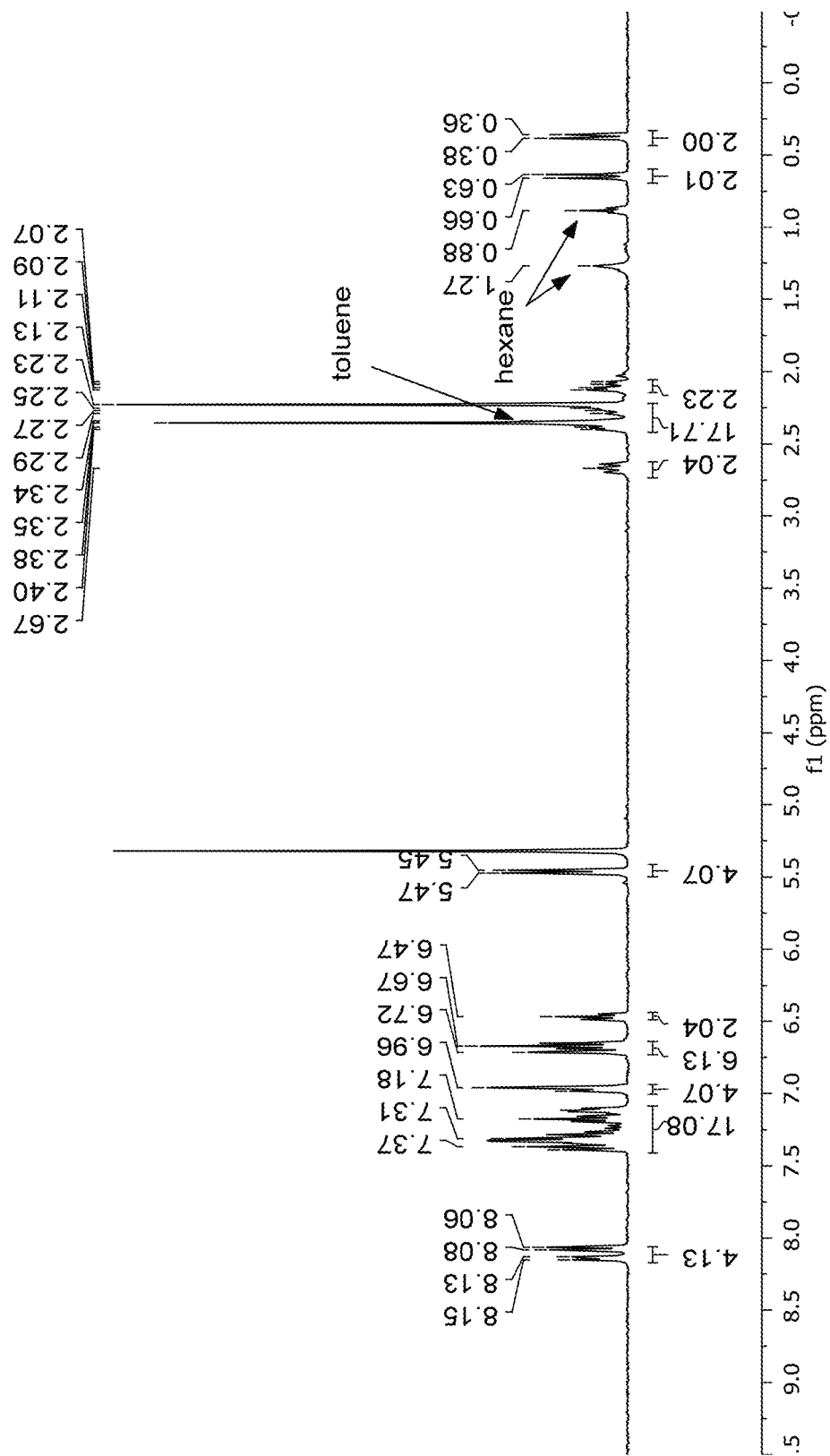
FIG. 9 is the $^1$HNMR spectrum for compound 2-Hf in $CD_2Cl_2$.
Figure 12:
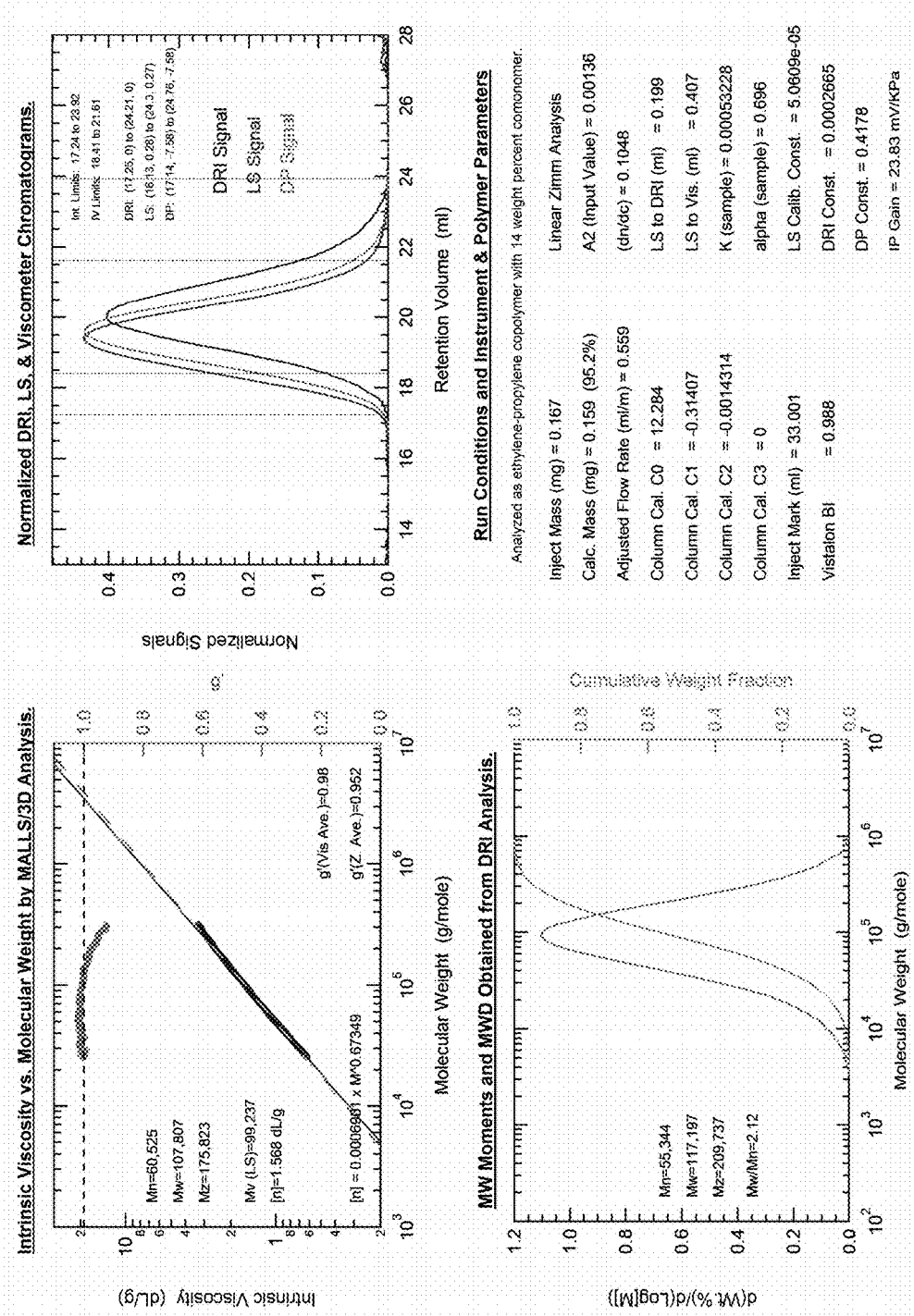
FIG. 12 is the GPC data for Table 6, Entry 6 (catalyst=1-Zr; polymer=EP).

FIG. 3 shows the chain transfer efficiency of 1-Hf (data from Table 14, Entries 1-24). The equation and coefficient of determination of the linear fits (least squared fit, Microsoft™ Excel 2010) are included in the figure. The slope of the linear fit corresponds to the number of chains transferred to the CTA metal (per metal). The figure shows that diethylzinc is an effective CTA with 1-Hf.

Additional GPC Analysis for Selected Polymer Samples. Mw, Mn, and Mw/Mn are determined by using a High Temperature Size Exclusion Chromatograph (Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, pp. 6812-6820, (2001), and references therein. Three Polymer Laboratories PLgel 10 μm Mixed-B LS columns are used. The nominal flow rate is 0.5 mL/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on at least 1 to 1.5 hours before running the samples. The concentration, c, at each point in the chromatogram is calculated from the baseline-subtracted DRI signal, IDRI, using the following equation:

$$c = K_{DRI} I_{DRI}/(dn/dc)$$

where KDRI is a constant determined by calibrating the DRI, and (dn/dc) is the refractive index increment for the system. The refractive index, n=1.500 for TCB at 145° C. and λ=660 nm. Units on parameters throughout this description of the GPC-SEC method are such that concentration is expressed in g/cm3, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c.$$

Here, $\Delta R(\theta)$ is the measured excess Rayleigh scattering intensity at scattering angle $\theta$, c is the polymer concentration determined from the DRI analysis, $A_2$ is the second virial coefficient, for purposes of this invention $A_2=0.0006$, (dn/dc) is the refractive index increment for the system. $P(\theta)$ is the form factor for a monodisperse random coil, and $K_o$ is the optical constant for the system:

$$K_o = \frac{4\pi^2 n^2 (dn/dc)^2}{\lambda^4 N_A}$$

where NA is Avogadro's number, and (dn/dc) is the refractive index increment for the system. The refractive index, n=1.500 for TCB at 145° C. and $\lambda$=660 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [$\eta$], at each point in the chromatogram is calculated from the following equation:

$$\eta_s = c[\eta] + 0.3(c[\eta])^2$$

where c is concentration and was determined from the DRI output.

The branching index ($g'_{vis}$) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits.

The branching index g'vis is defined as:

$$g'vis = \frac{[\eta]_{avg}}{kM_v^\alpha}$$

where, for purpose of this invention and claims thereto, $\alpha$=0.695 and k=0.00579 for linear ethylene polymers, $\alpha$=0.705 k=0.000262 for linear propylene polymers, and $\alpha$=0.695 and k=0.000181 for linear butene polymers. My is the viscosity-average molecular weight based on molecular weights determined by LS analysis. See Macromolecules, 2001, 34, 6812-6820 and Macromolecules, 2005, 38, 7181-7183, for guidance on selecting a linear standard having similar molecular weight and comonomer content, and determining k coefficients and $\alpha$ exponents.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. The term "comprising" is considered synonymous with the term "including." Likewise, whenever a composition, an element, or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A ligand represented by the formula (A):

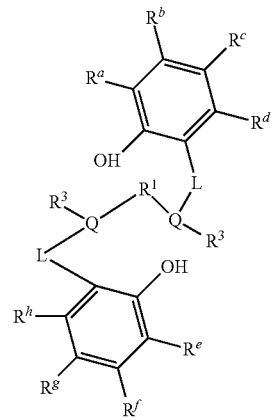

where each Q is neutral donor group comprising at least one atom from Group 15 or Group 16, and $R^3$ is not present when Q is a Group 16 atom;

each L is independently

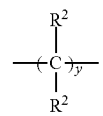

and is not part of an aromatic ring;

y is greater than or equal to 2;

$R^1$ is a divalent $C_1$-$C_{40}$ hydrocarbyl radical or divalent substituted hydrocarbyl radical comprising a portion that comprises a linker backbone comprising from 1 to 18 carbon atoms linking or bridging between the two Q groups;

each $R^a$, $R^b$, $R^c$, $R^d$, $R^e$, $R^f$, $R^g$, and $R^h$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;

each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic; and each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group.

2. A transition metal complex represented by the formula (I):

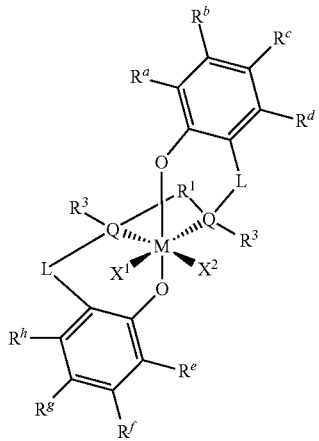

wherein M is a Group 4 transition metal;

each Q is neutral donor group comprising at least one atom from Group 15 or Group 16, and $R^3$ is not present when Q is a Group 16 atom;

each L is independently

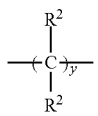

and is not part of an aromatic ring;

y is greater than or equal to 2;

$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic or heterocyclic structure;

$R^1$ is a divalent $C_1$-$C_{40}$ hydrocarbyl radical or divalent substituted hydrocarbyl radical comprising a portion that comprises a linker backbone comprising from 1 to 18 carbon atoms linking between the two Q groups;

each $R^a$, $R^b$, $R^c$, $R^d$, $R^e$, $R^f$, $R^g$, and $R^h$ is, independently, a hydrogen, a $C_1$-$C_{60}$ hydrocarbyl radical, a $C_1$-$C_{40}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;

each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic or polycyclic ring structure is not aromatic; and each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group.

3. A transition metal complex represented by the formula (II)

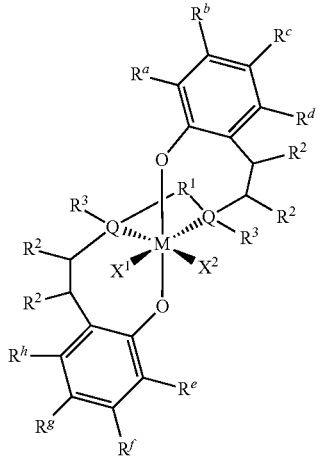

wherein M is a Group 4 transition metal;

each Q is neutral donor group comprising at least one atom from Group 15 or Group 16, and $R^3$ is not present when Q is a Group 16 atom;

$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic or heterocyclic structure;

$R^1$ is a divalent $C_1$-$C_{40}$ hydrocarbyl radical or divalent substituted hydrocarbyl radical comprising a portion that comprises a linker backbone comprising from 1 to 18 carbon atoms linking between the two Q groups;

each $R^a$, $R^b$, $R^c$, $R^d$, $R^e$, $R^f$, $R^g$, and $R^h$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof;

each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic, polycyclic or heterocyclic structure is not aromatic; and each $R^3$ is, independently, a hydrogen, a $C_1$-$C_{40}$ hydrocarbyl radical, a $C_1$-$C_{40}$ substituted hydrocarbyl radical, a heteroatom or a heteroatom-containing group.

4. The transition metal complex of claim 2, wherein $R^a$ and $R^e$ are carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl.

5. The transition metal complex of claim 2, wherein Q is a neutral donor group comprising at least one atom from Group 15 or Group 16 and the -(-Q-$R^1$-Q-)-fragment can form a substituted or unsubstituted heterocycle which may or may not be aromatic and may have multiple fused rings.

6. The transition metal complex of claim 2, wherein each $R^a$, $R^b$, $R^c$, $R^d$, $R^e$, $R^f$, $R^g$, and $R^h$ is independently a hydrogen, a $C_1$-$C_{20}$ hydrocarbyl radical, or a $C_1$-$C_{20}$ substituted hydrocarbyl radical.

7. The transition metal complex of claim 2, wherein M is Hf or Zr.

8. The transition metal complex of claim 2, wherein Q is O, N, S, or P.

9. The transition metal complex of claim 2, wherein $R^a$ is carbazolyl or substituted carbazolyl and $R^e$ is carbazolyl or substituted carbazolyl.

10. The transition metal complex of claim 2, wherein $R^1$ is a divalent $C_1$-$C_{20}$ hydrocarbyl radical or divalent substituted hydrocarbyl radical comprising a portion that comprises a linker backbone comprising from 1 to 18 carbon atoms linking or bridging between the two Q groups.

11. A catalyst system comprising activator and the complex of claim 2.

12. The catalyst system of claim 11, wherein the catalyst system further comprises a chain transfer agent.

13. The catalyst system of claim 11, wherein the catalyst system further comprises a chain transfer agent represented by the formula $R_3Al$ or $R_2Zn$, where R is a $C_1$ to $C_{20}$ alkyl group.

14. The catalyst system of claim 11, wherein the activator is an alumoxane.

15. The catalyst system of claim 11, wherein the activator is a non-coordinating anion.

16. The catalyst system of claim 11, wherein the activator is selected from the group consisting of: methylalumoxane, ethylalumoxane, isobutyl alumoxane, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis (3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl) phenyl)borate, triphenylcarbenium tetra(perfluorophenyl) borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, and 4-(tris(pentafluorophenyl)borate)-2,3,5,6-tetrafluoropyridine.

17. A polymerization process to produce polyolefin comprising:
a) contacting one or more olefin monomers with the catalyst system of claim 11, and
b) recovering olefin polymer.

18. The process of claim 17, wherein the monomer comprises ethylene and/or propylene.

19. The process of claim 17, wherein the transition metal complex is supported.

20. A polymerization process to produce polyolefin comprising:
a) contacting one or more olefin monomers with the catalyst system comprising activator, the transition metal complex of claim 2, and a chain transfer agent represented by the formula $R_3Al$ or $R_2Zn$, where R is a $C_1$ to $C_{20}$ alkyl group, and
b) recovering olefin polymer,
where the chain transfer agent is present at a molar ratio of the metal of the transition metal complex to the metal of the chain transfer agent of at least 10:1.

21. The process of claim 17, wherein the process is a continuous process.

22. The process of claim 17, wherein step a) occurs at a temperature of at least 70° C.

23. The process of claim 17, wherein hydrogen is present in step a).

24. The process of claim 17, wherein hydrogen and a chain transfer agent are present in step a).

25. A transition metal complex represented by the formula:

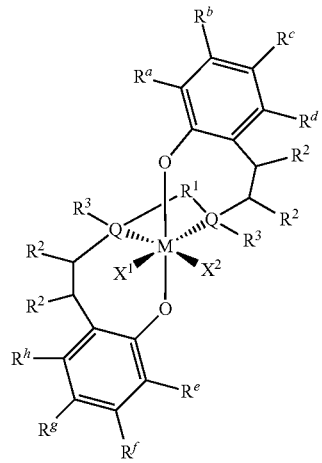

wherein $X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic, polycyclic or heterocyclic structure;

$R^1$ is a divalent $C_1$-$C_{40}$ hydrocarbyl radical or divalent substituted hydrocarbyl radical comprising a portion that comprises a linker backbone comprising from 1 to 18 carbon atoms linking or bridging between the two Q groups;

each $R^a$ and $R^e$ is, independently, phenyl or substituted phenyl;

each $R^b$, $R^c$, $R^d$, $R^f$, $R^g$, and $R^h$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more of $R^a$ to $R^h$ may independently join together to form a $C_4$ to $C_{62}$ cyclic, polycyclic or heterocyclic structure, or a combination thereof; and each $R^2$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more adjacent $R^2$ groups may independently join together to form a $C_4$ to $C_{62}$ cyclic or polycyclic ring structure, or a combination thereof, provided that such cyclic, polycyclic or heterocyclic structure is not aromatic.

26. The transition metal complex of claim 1, wherein Q is $NR'_2$, $OR'$, $SR'$, $PR'_2$, where R'is as defined for $R^a$.

27. The transition metal complex of claim 3 wherein, wherein M is Hf or Zr; Q is O, N, S, or P; $R^a$ is carbazolyl or substituted carbazolyl; $R^e$ is carbazolyl or substituted carbazolyl; and $R^1$ is a divalent $C_1$-$C_{20}$ hydrocarbyl radical or divalent substituted hydrocarbyl radical comprising a portion that comprises a linker backbone comprising from 1 to 18 carbon atoms linking or bridging between the two Q groups.

28. A catalyst system comprising an activator and the complex of claim 3.

29. A catalyst system comprising the transition metal complex of claim 27 and an activator.

30. The process of claim 17, wherein the activator is selected from the group consisting of: methylalumoxane, ethylalumoxane, isobutyl alumoxane, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis (3,5-bis(trifluoromethyl)phenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl)phenyl)borate, triphenylcarbenium tetra(perfluorophenyl) borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, and 4-(tris (pentafluorophenyl)borate)-2,3,5,6-tetrafluoropyridine.

31. The process of claim 30, wherein the process is a continuous process; step a) occurs at a temperature of at least 70° C.; and hydrogen is present in step a).

32. The process of claim 30, wherein hydrogen and a chain transfer agent are present in step a).

33. A process to produce polyolefin comprising:
a) contacting one or more olefin monomers with the catalyst system of claim 11, and
b) recovering olefin polymer.

34. The process of claim 33, wherein the process is a continuous process; step a) occurs at a temperature of at least 70° C.; hydrogen is present in step a); and hydrogen and chain transfer agent are present in step a).

35. The transition metal complex of claim 2, wherein $R^a$ and $R^e$ are carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl, and $R^a$ and $R^e$ are the same.

* * * * *